US007825263B2

United States Patent
Del Soldato et al.

(10) Patent No.: US 7,825,263 B2
(45) Date of Patent: Nov. 2, 2010

(54) NITROOXYDERIVATIVES OF CARVEDILOL AND OTHER BETA BLOCKERS AS ANTIHYPERTENSIVE

(75) Inventors: Piero Del Soldato, Monza (IT); Francesca Benedini, Milan (IT); Ennio Ongini, Segrate (IT)

(73) Assignee: Nicox S.A., Sophia Antipolis - Valbonne (FR)

( * ) Notice: Subject to any disclaimer, the term of this patent is extended or adjusted under 35 U.S.C. 154(b) by 1002 days.

(21) Appl. No.: 10/577,912

(22) PCT Filed: Dec. 1, 2004

(86) PCT No.: PCT/EP2004/013683

§ 371 (c)(1), (2), (4) Date: Sep. 13, 2006

(87) PCT Pub. No.: WO2005/053685

PCT Pub. Date: Jun. 16, 2005

(65) Prior Publication Data

US 2007/0072854 A1    Mar. 29, 2007

(30) Foreign Application Priority Data

Dec. 2, 2003   (EP)  ................... 03104484

(51) Int. Cl.
*C07D 209/82*   (2006.01)
*A61K 31/403*   (2006.01)
(52) U.S. Cl. ...................... 548/444; 514/411
(58) Field of Classification Search ........... 548/444; 514/411
See application file for complete search history.

(56) References Cited

U.S. PATENT DOCUMENTS

| 4,801,596 | A | | 1/1989 | Simon et al. |
| 5,502,237 | A | | 3/1996 | Prat Quin et al. |
| 5,639,904 | A | | 6/1997 | Prat Quinones et al. |
| 5,932,538 | A | * | 8/1999 | Garvey et al. .......... 514/2 |
| 6,242,432 | B1 | | 6/2001 | Del Soldato |

FOREIGN PATENT DOCUMENTS

| EP | 0 200 915 A | 11/1986 |
| EP | 0 637 583 A | 2/1995 |
| WO | 98/21193 A | 5/1998 |

OTHER PUBLICATIONS

CAPLUS abstract of GB 707293.*
Yamamoto et al., Exper. Biol. and Medicine, 225 (3): p. 200-206 (2000).*
Jayachandran et al., "Up-regulation of endothelial nitric oxide synthase through beta2-adrenergic receptor: The role of a beta-blocker with NO-releasing action", Biochemical and Biophysical Research Communications, 2001, pp. 589-594, vol. 280, No. 3.

* cited by examiner

*Primary Examiner*—Robert Havlin
(74) *Attorney, Agent, or Firm*—Arent Fox LLP

(57) ABSTRACT

The present invention relates to β-adrenergic blockers nitrooxyderivatives of general formula (I):

$$A\text{-}(Y\text{—}ONO_2)_s$$

and enantiomers and diastereoisomers and pharmaceutically acceptable salts thereof, pharmaceutical compositions containing them and their use for the treatment of hypertension, cardiovascular diseases, glaucoma, migraine headache and vascular diseases.

16 Claims, No Drawings

NITROOXYDERIVATIVES OF CARVEDILOL AND OTHER BETA BLOCKERS AS ANTIHYPERTENSIVE

The present invention relates to β-adrenergic blockers derivatives. More particularly, the present invention relates to β-adrenergic blockers nitrooxyderivatives, pharmaceutical compositions containing them and their use for the treatment of hypertension, cardiovascular diseases, glaucoma, migraine headache, vascular diseases and elevated intraocular pressure.

β-adrenergic blockers (β-blockers) are widely used in the treatment of hypertension and cardiovascular diseases including angina pectoris, arrhythmias, acute myocardial infarction, hypertrophic cardiomyopathy, congestive heart failure.

They work to block the effects of catecholamines at receptor sites in the heart, but they differ somewhat in their ability to block receptors in the blood vessels and lungs. Selective β-blockers have their major actions on the heart, some others are weak stimulators of the β-receptor while still blocking the major actions of catecholamines, some block both the $β_1$ and $β_2$ receptors in the heart and those in the blood vessels and have no stimulatory activity and some block other cathecolamine receptors that can lead to further vascular effects on blood vessels.

Several side effects are associated with this class of drugs such as muscle fatigue, sleep disturbances, decreased heart rate, hypotension, cold extremities, bronchospasm in asthmatic patients, hypoglycemia, increased in plasma lipids.

Moreover, abrupt withdrawal after long-term treatment with β-blockers has to be avoided, because an increased sensitivity to β-adrenergic system develops U.S. Pat. No. 6,242,432 discloses derivatives of formula $A-(X_1—NO_2)_{to}$ having an antithrombotic activity, wherein A is the residue of a β-adrenergic blocker, $X_1$ is a bivalent connecting bridge and $t_o$ is 1 or 2. The invention is limited to particular residues of β-adrenergic blockers.

U.S. Pat. No. 5,502,237 and U.S. Pat. No. 5,639,904 disclose derivatives of formula $R_1$—Ar—O—$CH_2$—CH(OH)—$CH_2$—NH—CH($CH_3$)$_2$ used for the treatment of cardiovascular affections, wherein $R_1$ is a chain having at least one nitrooxy group as substituent.

U.S. Pat. No. 4,801,596 discloses aminopropanol derivatives of formula

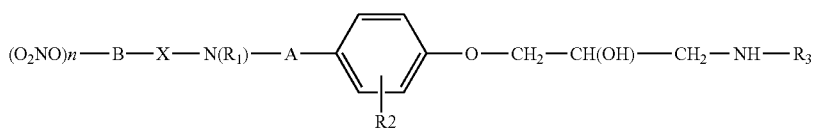

that can be used for prophylaxis and/or treatment of heart and circulatory diseases, wherein $R_3$ is an alkyl or a nitrooxyalkyl radical containing 3 to 8 carbon atoms.

It was an object of the present invention to provide new β-adrenergic blockers nitrooxyderivatives having a significantly improved overall pharmacological profile as compared to native β-blockers that are able not only to eliminate or at least reduce the side effects associated with their parent compounds, but also having an improved pharmacological activity and tolerability.

It has been so surprisingly found that the β-adrenergic blockers nitrooxyderivatives of the present invention have a better pharmacological activity and organ protection properties, enhanced effects as anti-inflammatory, and on renal functions. In addition, they are effective in other pathologies including atherosclerosis, diabetes, peripheral vascular diseases (PVD) and elevated intraocular pressure.

In particular, it has been recognized that the β-adrenergic blockers nitrooxyderivatives of the present invention, differently from the above mentioned compounds of the prior art, exhibit an improved activity on the cardiovascular system and enhanced tolerability and can be employed for treating or preventing hypertension, cardiovascular diseases, glaucoma, migraine headache, vascular diseases and elevated intraocular pressure.

Object of the present invention are β-adrenergic blockers nitrooxyderivatives of general formula (I):

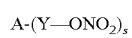

A-(Y—$ONO_2$)$_s$ and enantiomers and diastereoisomers and pharmaceutically acceptable salts thereof, wherein s is an integer equal to 1 or 2;

A is selected from the following β-adrenergic blocker residues of formula (II):

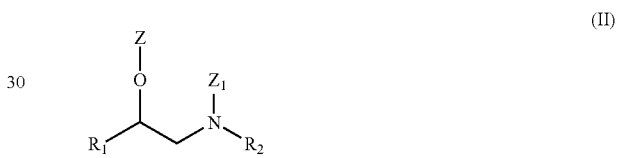

(II)

wherein
$R_1$ is selected from the group consisting of:

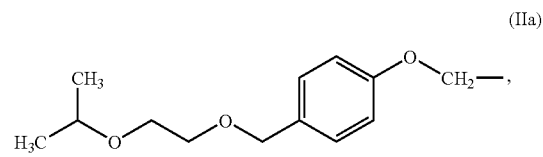

(IIa)

-continued

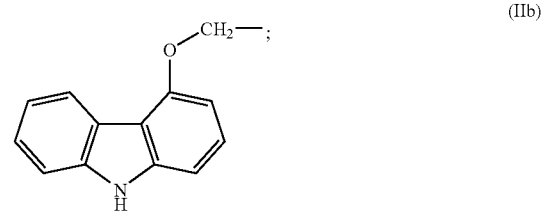

(IIb)

-continued (IIc) 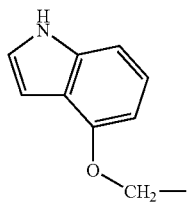

(IId) 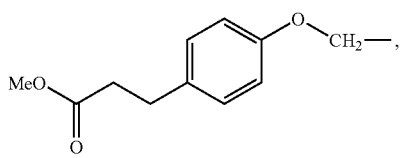

(IIe) 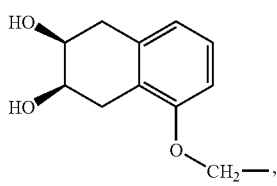

(IIf) 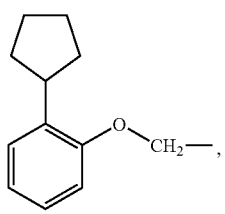

(IIg) 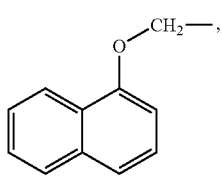

(IIh) 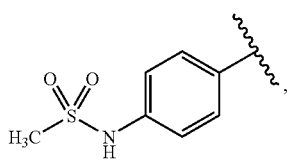

(IIi) 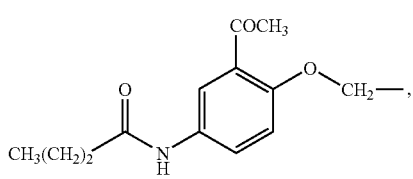

(IIL) 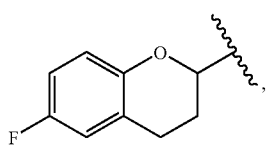

(IIm) 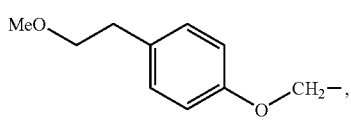

-continued (IIn) 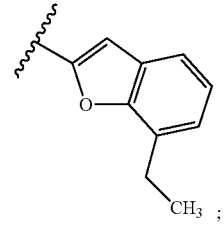

$R_2$ is selected from the group consisting of: —CH(CH$_3$)$_2$, —C(CH$_3$)$_3$ or (IIIa) 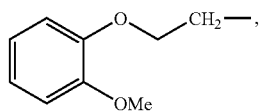

(IIIb) 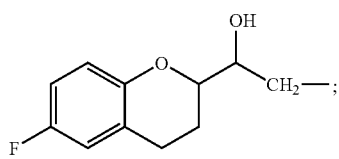

when the radical $R_1$ has chosen from the formulae (IIa), (IIc), (IId), (IIg), (IIh), (IIi), (IIm), $R_2$ is —CH(CH$_3$)$_2$;

when the radical $R_1$ has chosen from the formulae (IIe), (IIf) or (IIn), $R_2$ is —C(CH$_3$)$_3$;

when $R_1$ is the radical (IIb), $R_2$ is (IIIa);

when $R_1$ is the radical (IIL), $R_2$ is (IIIb);

Z is H or is a group capable of binding Y selected from the group consisting of:

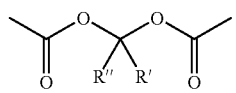

wherein R' and R'' are the same or different, and are H or straight or branched $C_1$-$C_4$ alkyl;

$Z_1$ is H or a —C(O)— capable of binding Y;

with the proviso that when s of formula (I) is 1, Z or $Z_1$ is H;

preferably when s of formula (I) is 2, Z and $Z_1$ are —C(O)—;

Y is a bivalent radical having the following meanings:

a)

straight or branched $C_1$-$C_{20}$ alkylene, preferably $C_1$-$C_{10}$ alkylene, more preferably $C_3$-$C_6$ alkylene, being optionally substituted with one or more of the substituents selected from the group consisting of: halogen atoms, hydroxy, —ONO$_2$ or T, wherein T is —OC(O)($C_1$-$C_{10}$alkyl)-ONO$_2$, —O($C_1$-$C_{10}$alkyl)-ONO$_2$;

b)

cycloalkylene with 5 to 7 carbon atoms into cycloalkylene ring, the ring being optionally substituted with side chains $T_1$, wherein $T_1$ is straight or branched alkyl with from 1 to 10 carbon atoms, $T_1$ is preferably CH$_3$;

c)

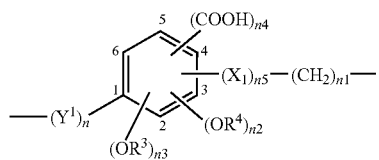
(IV)

wherein:
n is an integer from 0 to 20, preferably n is an integer from 0 to 10, more preferably n is 0 or 1,
n1 is an integer from 1 to 20, preferably from 1 to 10, more preferably n1 is 1;
n2, n3, n4 and n5 are integers equal or different from one another, equal to 0 or 1;
$R^3$ and $R^4$ are independently selected from H or $CH_3$;
$Y^1$ is —$CH_2$— or —$(CH_2)_{na}$—CH=CH— wherein na is an integer from 0 to 20, preferably na is equal to 0;
$X_1$ is —WC(O)— or —C(O)W—, wherein W is oxygen, sulfur or NH, preferably W is oxygen;

d)

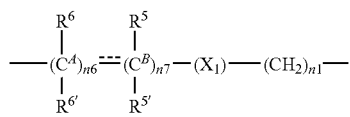
(V)

wherein:
n1 is an integer from 1 to 20, preferably from 1 to 10;
$X_1$ is —WC(O)— or —C(O)W—, wherein W is oxygen, sulfur or NH, preferably W is sulfur or NH,
n6 is an integer from 1 to 20, preferably from 1 to 5, more preferably n6 is 1,
n7 is an integer from 0 to 20, preferably from 0 to 5, more preferably n7 is 1,
$R^5$, $R^{5'}$, $R^6$ and $R^{6'}$ are independently selected from the group consisting of: H, $CH_3$, OH, $NH_2$, $NHCOCH_3$, COOH, $CH_2SH$ and $C(CH_3)_2SH$;
when the bond between the $C^A$ and $C^B$ carbons is a double bond $R^5$ and $R^6$ or $R^{6'}$ and $R^{5'}$ are absent;
with the proviso that when Y is selected from the bivalent radicals mentioned under c)-d), the —$ONO_2$ group is linked to the —$(CH_2)_{n1}$— group;

e)

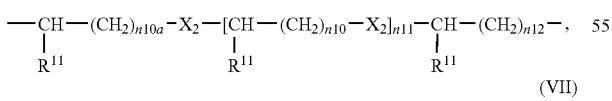
(VI)

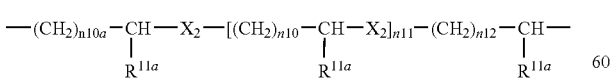
(VII)

wherein $X_2$ is O or S,
n10a, n10 and n12 are integer independently selected from 0 to 20,
n10a is preferably selected from 0 to 10, more preferably n10a is 0 or 1, n10 and n12 are preferably selected from 1 to 10, more preferably n10 and n12 are 1 or 2
n11 is an integer from 0 to 6, preferably from 0 to 4, more preferably n11 is 0 or 1,
$R^{11}$ is H, $CH_3$ or nitrooxy group, preferably $R^{11}$ is H or a nitrooxy group and
$R^{11a}$ is $CH_3$ or nitrooxy group;

f)

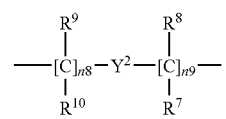
(VIII)

wherein
n8 is an integer from 0 to 10;
n9 is an integer from 1 to 10;
$R^9$, $R^{10}$, $R^8$, $R^7$ are same or different, and are H or straight or branched $C_1$-$C_4$ alkyl, preferably $R^9$, $R^{10}$, $R^8$, $R^7$ are H;
wherein the —$ONO_2$ group is linked to

wherein n9 is as defined above;
$Y^2$ is an heterocyclic saturated, unsaturated or aromatic 5 or 6 members ring, containing one or more heteroatoms selected from nitrogen, oxygen, sulfur,
and is selected from the group consisting of

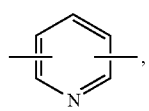
(Y1)

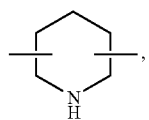
(Y2)

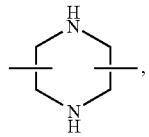
(Y3)

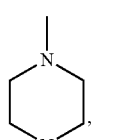
(Y4)

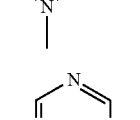
(Y5)

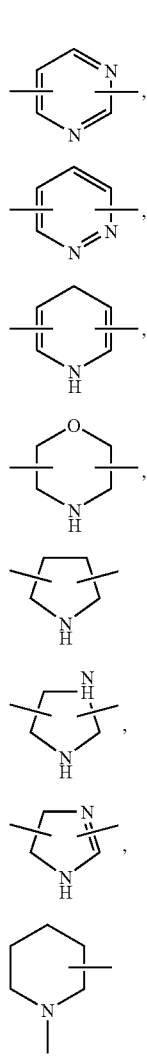
(Y6), (Y7), (Y8), (Y9), (Y10), (Y11), (Y12), (Y13)
One embodiment provides compounds of formula (I) wherein:
s is 2,
A is selected from the following β-adrenergic blocker residues of formula (II):
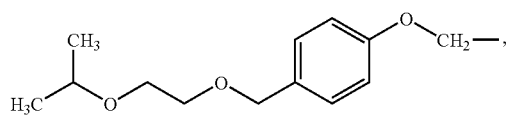
(II)
wherein
$R_1$ is selected from the group consisting of:
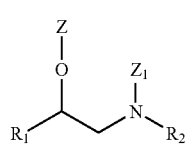
(IIa)
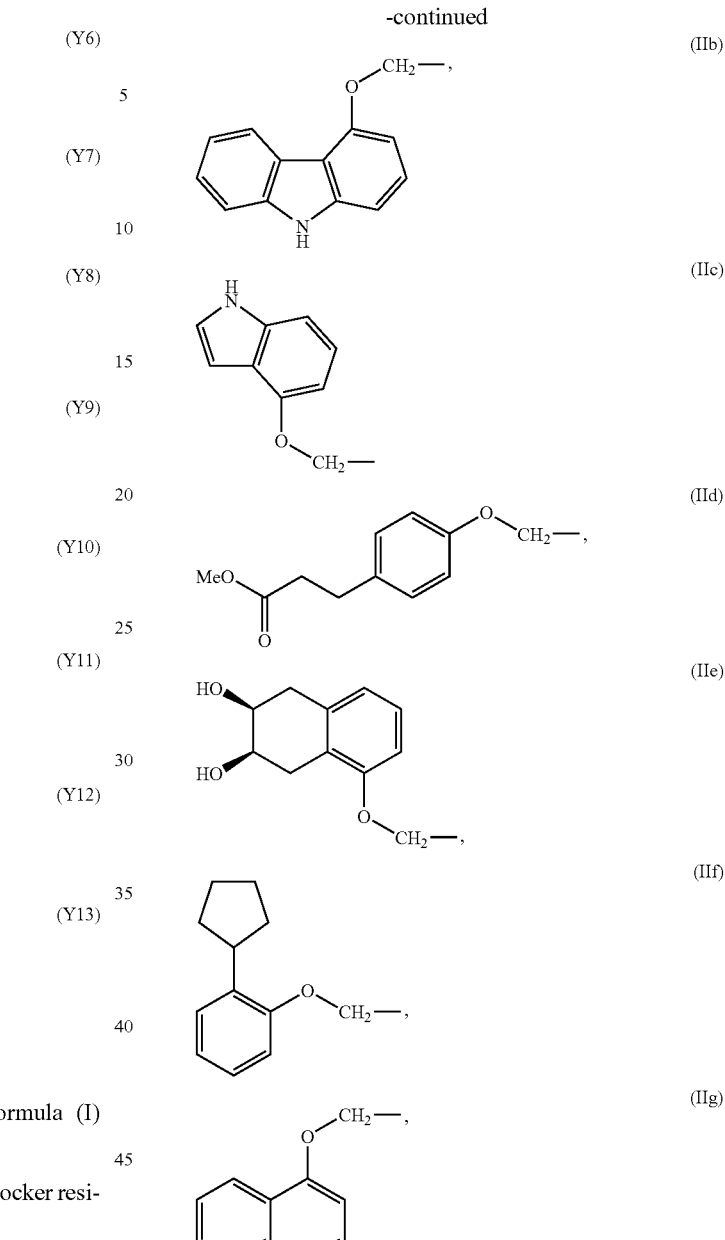
(IIb), (IIc), (IId), (IIe), (IIf), (IIg), (IIh)
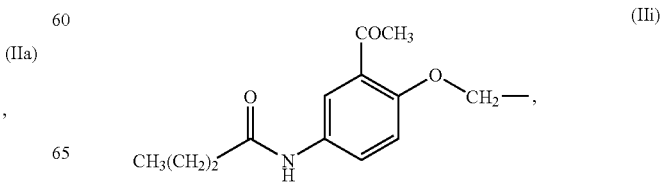
(IIi)

-continued

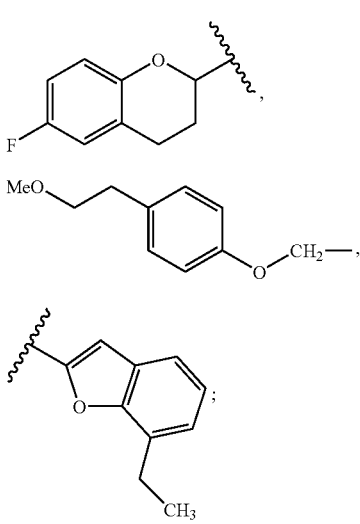

(IIL)

(IIm)

(IIn)

$R_2$ is selected from the group consisting of: —CH(CH$_3$)$_2$, —C(CH$_3$)$_3$ or

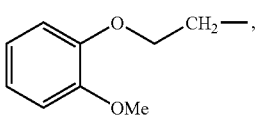

(IIIa)

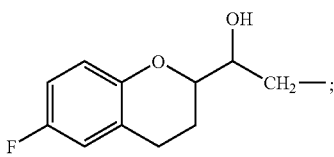

(IIIb)

when the radical $R_1$ has chosen from the formulae (IIa), (IIc), (IId), (IIg), (IIh), (IIi), (IIm), $R_2$ is —CH(CH$_3$)$_2$;
when the radical $R_1$ has chosen from the formulae (IIe), (IIf) or (IIn), $R_2$ is —C(CH$_3$)$_3$;
when $R_1$ is the radical (IIb), $R_2$ is (IIIa);
when $R_1$ is the radical (IIL), $R_2$ is (IIIb);

Z is a group capable of binding Y selected from the group consisting of:
—C(O)—, —C(O)O— or

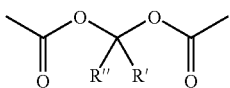

wherein R' and R" are the same or different, and are H or straight or branched $C_1$-$C_4$ alkyl;

$Z_1$ is H or a —C(O)— capable of binding Y, preferably Z and $Z_1$ are —C(O)—;

Y is a bivalent radical having the following meaning:

a)
straight or branched $C_1$-$C_{20}$ alkylene, preferably $C_1$-$C_{10}$ alkylene, more preferably $C_3$-$C_6$ alkylene, being optionally substituted with one or more of the substituents selected from the group consisting of: halogen atoms, hydroxy, —ONO$_2$ or T, wherein T is —OC(O)(C$_1$-C$_{10}$alkyl)-ONO$_2$, —O(C$_1$-C$_{10}$alkyl)-ONO$_2$;

b)
cycloalkylene with 5 to 7 carbon atoms into cycloalkylene ring, the ring being optionally substituted with side chains $T_1$, wherein $T_1$ is straight or branched alkyl with from 1 to 10 carbon atoms, $T_1$ is preferably CH$_3$;

c)

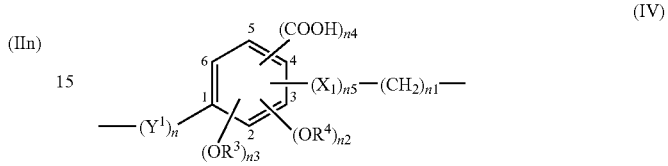

(IV)

wherein:
n is an integer from 0 to 20, preferably n is an integer from 0 to 10, more preferably n is 0 or 1,
n1 is an integer from 1 to 20, preferably from 1 to 10, more preferably n1 is 1;
n2, n3, n4 and n5 are integers equal or different from one another, equal to 0 or 1;
$R^3$ and $R^4$ are independently selected from H or CH$_3$;
$Y^1$ is —CH$_2$— or —(CH$_2$)$_{na}$—CH=CH— wherein na is an integer from 0 to 20, preferably na is equal to 0;
$X_1$ is —WC(O)— or —C(O)W—, wherein W is oxygen, sulfur or NH, preferably W is oxygen;

d)

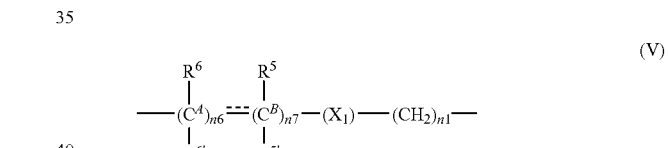

(V)

wherein:
n1 is an integer from 1 to 20, preferably from 1 to 10;
$X_1$ is —WC(O)— or —C(O)W—, wherein W is oxygen, sulfur or NH, preferably W is sulfur or NH;
n6 is an integer from 1 to 20, preferably from 1 to 5, more preferably n6 is 1,
n7 is an integer from 0 to 20, preferably from 0 to 5, more preferably n7 is 1,
$R^5$ and $R^{5'}$ $R^6$ and $R^{6'}$ are independently selected from the group consisting of: H, CH$_3$, OH, NH$_2$, NHCOCH$_3$, COOH, CH$_2$SH and C(CH$_3$)$_2$SH;
when the bond between the $C^A$ and $C^B$ carbons is a double bond $R^5$ and $R^6$ or $R^{6'}$ and $R^{5'}$ are absent;
with the proviso that when Y is selected from the bivalent radicals mentioned under c)-d), the —ONO$_2$ group is linked to the —(CH$_2$)$_{n1}$— group;

e)

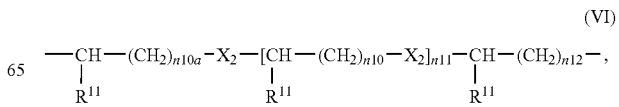

(VI)

-continued $$-(CH_2)_{n10a}-\underset{R^{11a}}{CH}-X_2-[(CH_2)_{n10}-\underset{R^{11a}}{CH}-X_2]_{n11}-(CH_2)_{n12}-\underset{R^{11a}}{CH}-\quad (VII)$$

wherein $X_2$ is O or S, n10a, n10 and n12 are integer independently selected from 0 to 20, n10a is preferably selected from 0 to 10, more preferably n10a is 0 or 1;

n10 and n12 are preferably selected from 1 to 10, more preferably n10 and n12 are 1 or 2;

n11 is an integer from 0 to 6, preferably from 0 to 4, more preferably n11 is 0 or 1;

$R^{11}$ is H, $CH_3$ or nitrooxy group, preferably $R^{11}$ is H or nitrooxy;

$R^{11a}$ is $CH_3$ or nitrooxy group;

f)

$$-\underset{R^{10}}{\overset{R^9}{[C]_{n8}}}-Y^2-\underset{R^7}{\overset{R^8}{[C]_{n9}}}- \quad (VIII)$$

wherein n8 is an integer from 0 to 10;

n9 is an integer from 1 to 10;

$R^9$, $R^{10}$, $R^8$, $R^7$ are same or different, and are H or straight or branched $C_1$-$C_4$ alkyl, preferably $R^9$, $R^{10}$, $R^8$, $R^7$ are H;

wherein the —$ONO_2$ group is linked to $$-[C]_{n9}$$

wherein n9 is as defined above;

$Y^2$ is an heterocyclic saturated, unsaturated or aromatic 5 or 6 members ring, containing one or more heteroatoms selected from nitrogen, oxygen, sulfur, and is selected from the group consisting of (Y1) pyridine, (Y2) piperidine, (Y3) piperazine, (Y4) N,N'-dimethylpiperazine, (Y5) pyrazine, (Y6) pyrimidine, (Y7) pyridazine, (Y8) tetrahydropyridine, (Y9) morpholine, (Y10) pyrrolidine, (Y11) imidazolidine, (Y12) imidazoline, (Y13) N-methylpiperidine, Another embodiment provides compounds of formula (I) wherein:

s is 1,

A is selected from the following β-adrenergic blocker residues of formula (II):

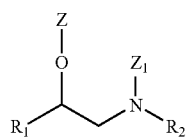

(II)

wherein

R₁ is selected from the group consisting of:

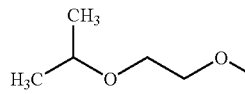

(IIa)

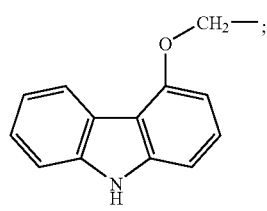

(IIb)

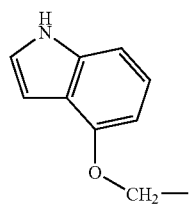

(IIc)

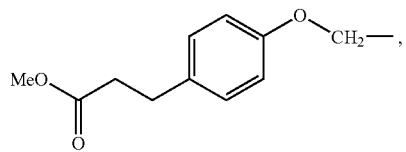

(IId)

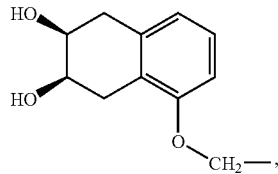

(IIe)

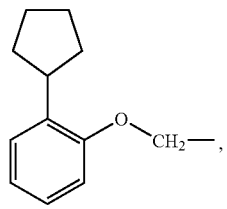

(IIf)

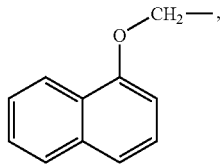

(IIg)

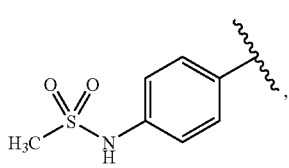

(IIh)

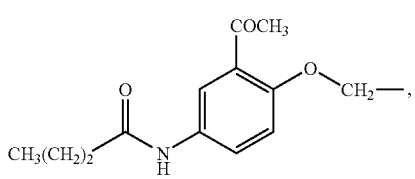

(IIi)

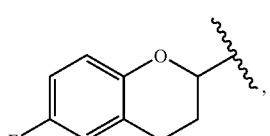

(IIL)

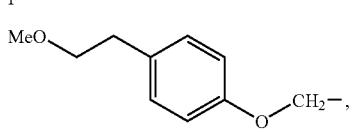

(IIm)

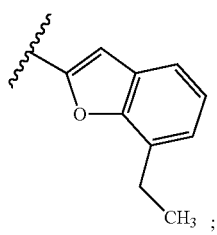

(IIn)

R₂ is selected from the group consisting of: —CH(CH₃)₂, —C(CH₃)₃ or

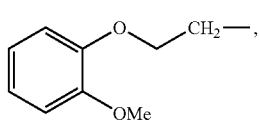

(IIIa)

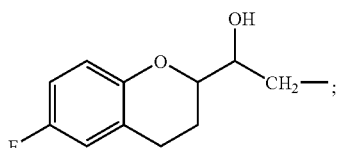

(IIIb)

when the radical R₁ has chosen from the formulae (IIa), (IIc), (IId), (IIg), (IIh), (IIi), (IIm), R₂ is —CH(CH₃)₂;

when the radical R₁ has chosen from the formulae (IIe), (IIf) or (IIn), R₂ is —C(CH₃)₃;

when R₁ is the radical (IIb), R₂ is (IIIa);

when R₁ is the radical (IIL), R₂ is (IIIb);

Z is H and Z₁ a —C(O)— capable of binding Y;

Y is a bivalent radical having the following meaning:

a) straight or branched $C_1$-$C_{20}$ alkylene, preferably $C_1$-$C_{10}$ alkylene, more preferably $C_3$-$C_6$ alkylene, being optionally substituted with one or more of the substituents selected from the group consisting of: halogen atoms, hydroxy, —$ONO_2$ or T, wherein T is —$OC(O)(C_1$-$C_{10}alkyl)$-$ONO_2$, —$O(C_1$-$C_{10}alkyl)$-$ONO_2$;

b) cycloalkylene with 5 to 7 carbon atoms into cycloalkylene ring, the ring being optionally substituted with side chains $T_1$, wherein $T_1$ is straight or branched alkyl with from 1 to 10 carbon atoms, $T_1$ is preferably $CH_3$;

c)

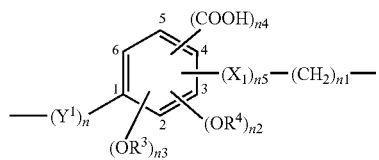
(IV)

wherein:

n is an integer from 0 to 20, preferably n is an integer from 0 to 10, more preferably n is 0 or 1, and n1 is an integer from 1 to 20, preferably from 1 to 10, more preferably n1 is 1;

n2, n3, n4 and n5 are integers equal or different from one another, equal to 0 or 1;

$R^3$ and $R^4$ are independently selected from H or $CH_3$;

$Y^1$ is —$CH_2$— or —$(CH_2)_{na}$—$CH=CH$— wherein na is an integer from 0 to 20, preferably na is equal to 0;

$X_1$ is —$WC(O)$— or —$C(O)W$—, wherein W is oxygen, sulfur or NH, preferably W is oxygen;

d)

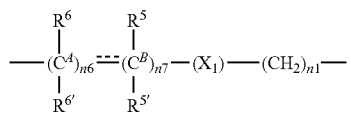
(V)

wherein:

n1 is an integer from 1 to 20, preferably from 1 to 10;

$X_1$ is —$WC(O)$— or —$C(O)W$—, wherein W is oxygen, sulfur or NH, preferably W is sulfur or NH;

n6 is an integer from 1 to 20, preferably from 1 to 5, more preferably n6 is 1, n7 is an integer from 0 to 20, preferably from 0 to 5, more preferably n7 is 1, $R^5$ and $R^{5'}$ $R^6$ and $R^{6'}$ are independently selected from the group consisting of: H, $CH_3$, OH, $NH_2$, $NHCOCH_3$, COOH, $CH_2SH$ and $C(CH_3)_2SH$;

when the bond between the $C^A$ and $C^B$ carbons is a double bond $R^5$ and $R^6$ or $R^{6'}$ and $R^{5'}$ are absent;

with the proviso that when Y is selected from the bivalent radicals mentioned under c)-d), the —$ONO_2$ group is linked to a —$(CH_2)_{n1}$— group;

e)

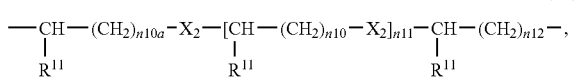
(VI)

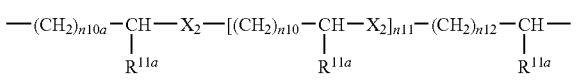
(VII)

wherein $X_2$ is O or S, n10a, n10 and n12 are integer independently selected from 0 to 20, n10a is preferably selected from 0 to 10, more preferably n10a is 0 or 1;

n10 and n12 are preferably selected from 1 to 10, more preferably n10 and n12 are 1 or 2;

n11 is an integer from 0 to 6, preferably from 0 to 4, more preferably n11 is 0 or 1;

$R^{11}$ is H, $CH_3$ or nitrooxy group, preferably $R^{11}$ is H or nitrooxy;

$R^{11a}$ is $CH_3$ or nitrooxy group;

f)

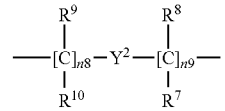
(VIII)

wherein n8 is an integer from 0 to 10;

n9 is an integer from 1 to 10;

$R^9$, $R^{10}$, $R^8$, $R^7$ are same or different, and are H or straight or branched $C_1$-$C_4$ alkyl, preferably $R^9$, $R^{10}$, $R^8$, $R^7$ are H;

wherein the —$ONO_2$ group is linked to

wherein n9 is as defined above;

$Y^2$ is an heterocyclic saturated, unsaturated or aromatic 5 or 6 members ring, containing one or more heteroatoms selected from nitrogen, oxygen, sulfur, and is selected from the group consisting of

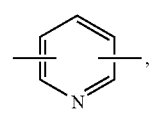
(Y1)

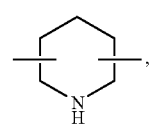
(Y2)

-continued
(Y3) 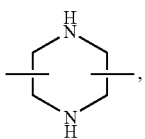
(Y4) 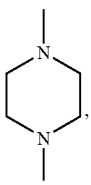
(Y5) 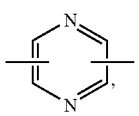
(Y6) 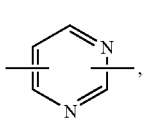
(Y7) 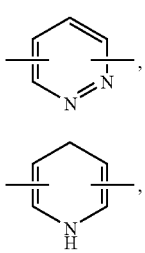
(Y8) 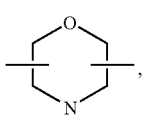
(Y9) 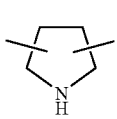
(Y10) 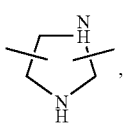
(Y11) 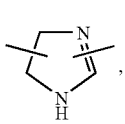
(Y12) 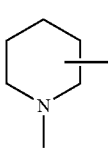
(Y13) 
Another embodiment provides compounds of formula (I) wherein s is 1, A is selected from the following β-adrenergic blocker residues of formula (II):
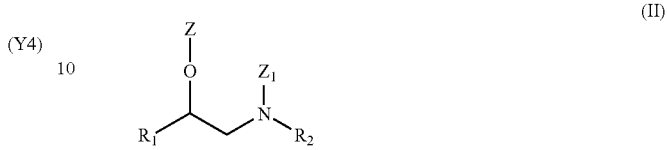
(II)
wherein
$R_1$ is selected from the group consisting of:
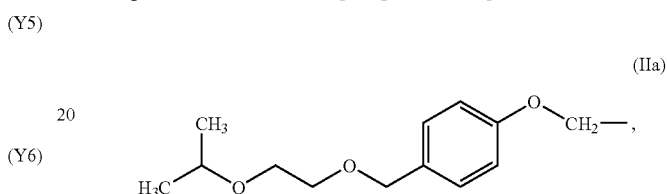
(IIa)
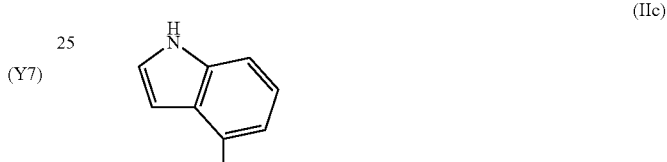
(IIc)
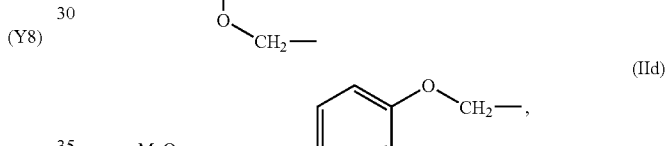
(IId)
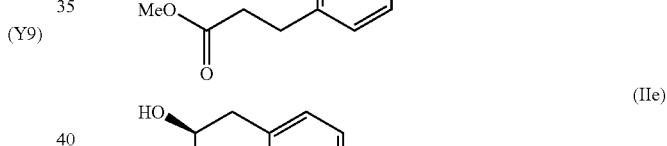
(IIe)
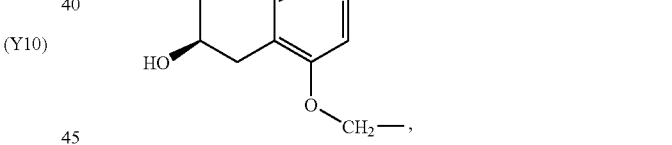
(IIf)
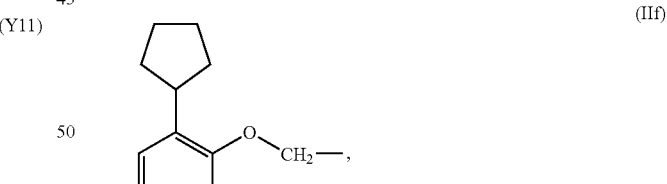
(IIg)
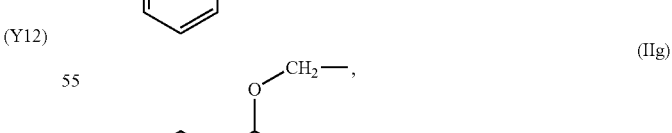
(IIh)
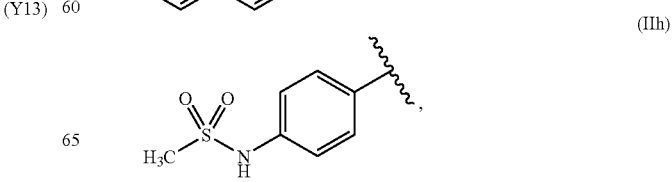

-continued (IIi)
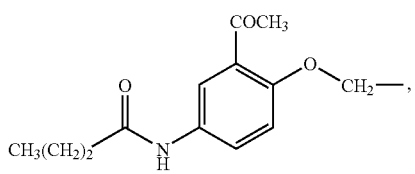

(IIL)
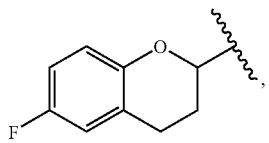

(IIm)
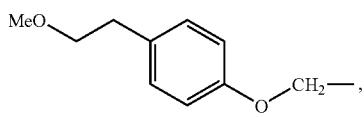

(IIn)
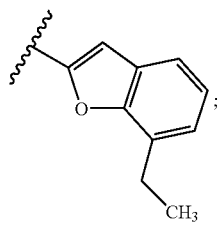

$R_2$ is selected from the group consisting of: —CH(CH$_3$)$_2$, —C(CH$_3$)$_3$ or (IIIb)
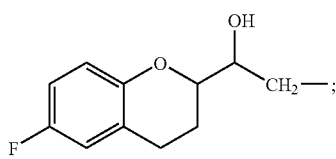

when the radical $R_1$ has chosen from the formulae (IIa), (IIc), (IId), (IIg), (IIh), (IIi), (IIm), $R_2$ is —CH(CH$_3$)$_2$;

when the radical $R_1$ has chosen from the formulae (IIe), (IIf) or (IIn), $R_2$ is —C(CH$_3$)$_3$;

when $R_1$ is the radical (IIL), $R_2$ is (IIIb);

$Z_1$ is H;

Z is a group capable of binding Y selected from the group consisting of:

—C(O)—, —C(O)O— or

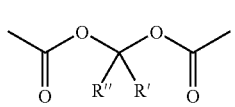

wherein R' and R" are the same or different, and are H or straight or branched $C_1$-$C_4$ alkyl;

Y is a bivalent radical having the following meaning:

c)

(IV)
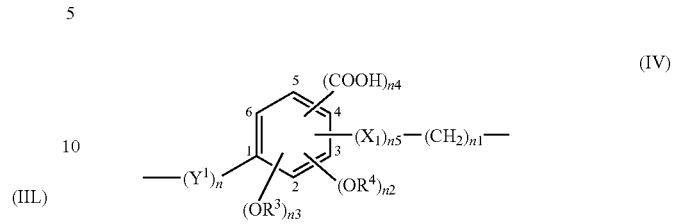

wherein:

n is an integer from 0 to 20, preferably n is an integer from 0 to 10, more preferably n is 0 or 1, n1 is an integer from 1 to 20, preferably from 1 to 10, more preferably n1 is 1;

n2, n3, n4 and n5 are integers equal or different from one another, equal to 0 or 1;

$R^3$ and $R^4$ are independently selected from H or CH$_3$;

$Y^1$ is —CH$_2$— or —(CH$_2$)$_{na}$—CH═CH— wherein na is an integer from 0 to 20, preferably na is equal to 0;

$X_1$ is —WC(O)— or —C(O)W—, wherein W is oxygen, sulfur or NH, preferably W is oxygen;

e)

(VI)
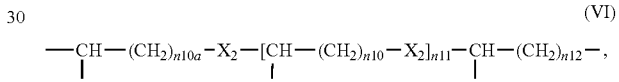

(VII)
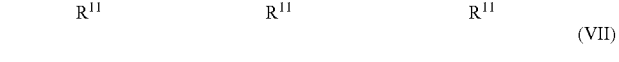

wherein $X_2$ is O or S, n10a is 0 or 1, n11 is 0 or 1, n10 and n12 are or 2;

$R^{11}$ is H, CH$_3$ or nitrooxy group;

$R^{11a}$ is CH$_3$ or nitrooxy group;

f)

(VIII)
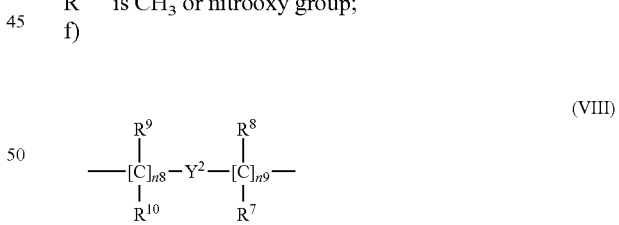

wherein n8 is an integer from 0 to 10;

n9 is an integer from 1 to 10;

$R^9$, $R^{10}$, $R^8$, $R^7$ are same or different, and are H or straight or branched $C_1$-$C_4$ alkyl, preferably $R^9$, $R^{10}$, $R^8$, $R^7$ are H;

wherein the —ONO$_2$ group is linked to

wherein n9 is as defined above;

$Y^2$ is an heterocyclic saturated, unsaturated or aromatic 5 or 6 members ring, containing one or more heteroatoms selected from nitrogen, oxygen, sulfur, and is selected from the group consisting of

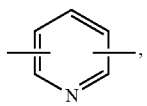
(Y1)

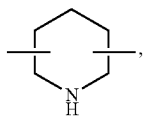
(Y2)

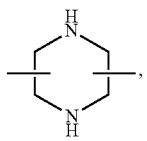
(Y3)

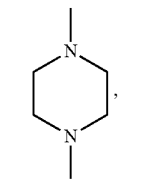
(Y4)

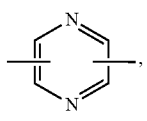
(Y5)

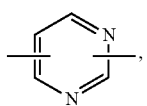
(Y6)

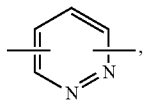
(Y7)

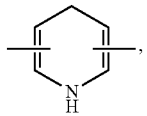
(Y8)

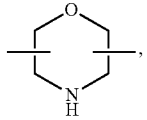
(Y9)

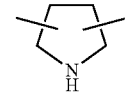
(Y10)

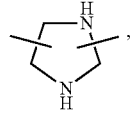
(Y11)

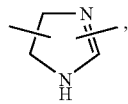
(Y12)

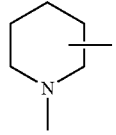
(Y13)

Another embodiment provides compounds of formula (I) wherein s is an integer equal to 1 or 2

A is the β-adrenergic blocker residue of formula (II):

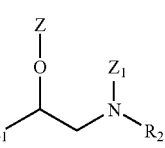
(II)

wherein $R_1$ is (IIb)

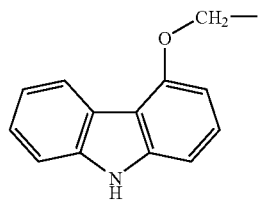
(IIb)

$R_2$ is (IIa)

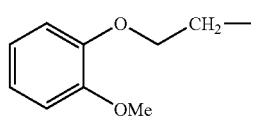
(IIIa)

Z is H or is a group capable of binding Y selected from the group consisting of:

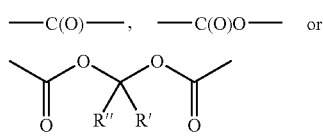

wherein R' and R" are the same or different, and are H or straight or branched $C_1$-$C_4$ alkyl;

$Z_1$ is H or a —C(O)— capable of binding Y;

with the proviso that when s of formula (I) is 1, Z or $Z_1$ is H;

preferably when s of formula (I) is 2, Z and $Z_1$ are —C(O)—;

Y is a bivalent radical having the following meaning:

a) straight or branched $C_1$-$C_{20}$ alkylene, preferably; $C_1$-$C_{10}$ alkylene, more preferably $C_3$-$C_6$ alkylene, being optionally substituted with one or more of the substituents selected from the group consisting of: halogen atoms, hydroxy, —$ONO_2$ or T, wherein T is —$OC(O)(C_1$-$C_{10}$alkyl)-$ONO_2$, —$O(C_1$-$C_{10}$alkyl)-$ONO_2$;

b) cycloalkylene with 5 to 7 carbon atoms into cycloalkylene ring, the ring being optionally substituted with side chains $T_1$, wherein $T_1$ is straight or branched alkyl with from 1 to 10 carbon atoms, $T_1$ is preferably $CH_3$;

c)

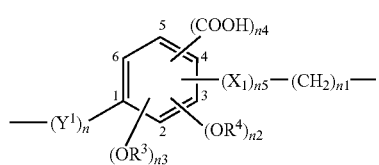
(IV)

wherein:

n is an integer from 0 to 20, preferably n is an integer from 0 to 10, more preferably n is 0 or 1, n1 is an integer from 1 to 20, preferably from 1 to 10, more preferably n1 is 1, n2, n3, n4 and n5 are integers equal or different from one another, equal to 0 or 1, $R^3$ and $R^4$ are independently selected from H or $CH_3$;

$Y^1$ is —$CH_2$— or —$(CH_2)_{na}$—CH=CH— wherein na is an integer from 0 to 20, preferably na is equal to 0;

$X_1$ is —WC(O)— or —C(O)W—, wherein W is oxygen, sulfur or NH, preferably W is oxygen;

d)

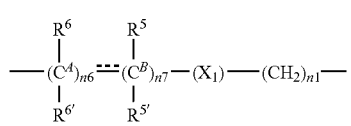
(V)

wherein:

n1 is an integer from 1 to 20, preferably from 1 to 10;

$X_1$ is —WC(O)— or —C(O)W—, wherein W is oxygen, sulfur or NH, preferably W is sulfur or NH;

n6 is an integer from 1 to 20, preferably from 1 to 5, more preferably n6 is 1, n7 is an integer from 0 to 20, preferably from 0 to 5, more-preferably n7 is 1, $R^5$ and $R^{5'}$ $R^6$ and $R^{6'}$ are independently selected from the group consisting of: H, $CH_3$, OH, $NH_2$, $NHCOCH_3$, COOH, $CH_2SH$ and $C(CH_3)_2SH$;

when the bond between the $C^A$ and $C^B$ carbons is a double bond $R^5$ and $R^6$ or $R^{6'}$ and $R^{5'}$ are absent;

with the proviso that when Y is selected from the bivalent radicals mentioned under c)-d), the —$ONO_2$ group is linked to a —$(CH_2)_{n1}$— group;

e)

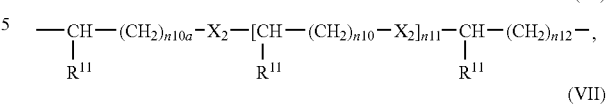
(VI)

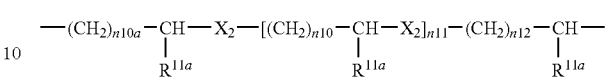
(VII)

wherein $X_2$ is O or S, n10a, n10 and n12 are integer independently selected from 0 to 20, n10a is preferably selected from 0 to 10, more preferably n10a is 0 or 1;

n10 and n12 are preferably selected from 1 to 10, more preferably n10 and n12 are 1 or 2, n11 is an integer from 0 to 6, preferably from 0 to 4, more preferably n11 is 0 or 1;

$R^{11}$ is H, $CH_3$ or nitrooxy group, preferably $R^{11}$ is H or a nitrooxy group, $R^{11a}$ is $CH_3$ or nitrooxy group;

f)

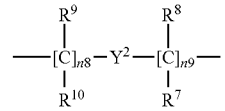
(VIII)

wherein n8 is an integer from 0 to 10;

n9 is an integer from 1 to 10;

$R^9$, $R^{10}$, $R^8$, $R^7$ are same or different, and are H or straight or branched $C_1$-$C_4$ alkyl, preferably $R^9$, $R^{10}$, $R^8$, $R^7$ are H;

wherein the —$ONO_2$ group is linked to

wherein n9 is as defined above;

$Y^2$ is an heterocyclic saturated, unsaturated or aromatic 5 or 6 members ring, containing one or more heteroatoms selected from nitrogen, oxygen, sulfur, and is selected from the group consisting of

(Y1)

(Y2)

-continued

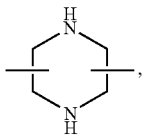
(Y3)

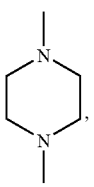
(Y4)

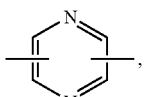
(Y5)

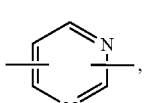
(Y6)

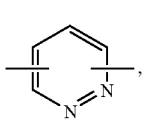
(Y7)

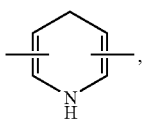
(Y8)

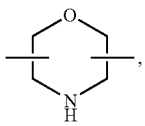
(Y9)

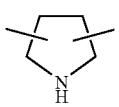
(Y10)

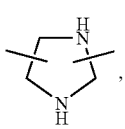
(Y11)

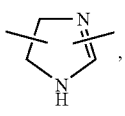
(Y12)

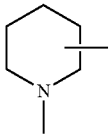
(Y13)

Preferred compounds are those of formula (I) wherein:

s is 2,

A is a β-adrenergic blocker residues of formula (II) as above defined

Z and $Z_1$ are —(CO)—

Y is a bivalent radical having the following meanings:
a) straight $C_1$-$C_{10}$ alkylene, preferably $C_3$-$C_6$ alkylene;
c)

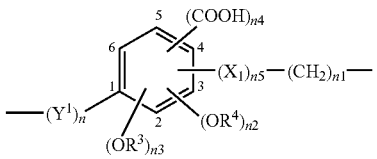
(IV)

wherein the —$ONO_2$ group is bound to $(CH_2)_{n1}$;

n, n2, n3, n4, n5 are equal to 0, n1 is 1 and the —$(CH_2)_{n1}$— group is bound to the phenyl ring through the $[C]_2$ or $[C]_3$ or $[C]_4$;

or n, n2, n5 are 1, n3 and n4 are equal to 0, and n1 is an integer from 1 to 10, $Y^1$ is —$(CH_2)_{na}$—CH=CH— wherein na is 0, $X_1$ is —WC(O)— wherein W is oxygen and the WC(O) group is bound to the phenyl ring through the $[C]_4$, $R^4$ is $CH_3$ and the ($OR^4$) group is bound to the phenyl ring through the $[C]_3$;

d)

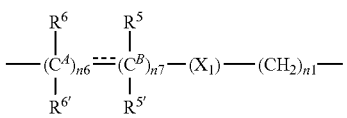
(V)

wherein n1 is an integer from 1 to 10, n6 and n7 are 1, $X_1$ is —WC(O)— wherein W is sulfur, $R^5$, $R^{5'}$ and $R^{6'}$ are H, $R^6$ is $NHCOCH_3$ and the —$ONO_2$ is bound to the —$(CH_2)_{n1}$— group;

e)

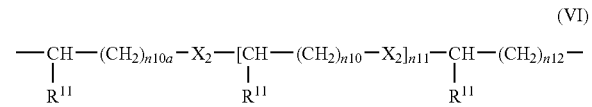
(VI)

wherein $X_2$ is O or S, and n11 is 0, n10a is an integer from 0 to 10, n12 is an integer from 1 to 10, $R^{11}$ is H or a nitrooxy group and the —$ONO_2$ group is bound to $(CH_2)_{n12}$;

Another group of preferred compounds comprises compounds of formula (I)

wherein s is 1,

A is a β-adrenergic blocker residues of formula (II) as above defined,

Z is H, $Z_1$ is —(CO)—

Y is a bivalent radical having the following meanings:
a) straight $C_1$-$C_{10}$ alkylene, preferably $C_3$-$C_6$ alkylene;

c)

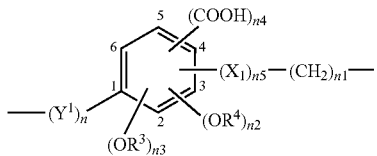
(IV)

wherein the —ONO$_2$ group is bound to (CH$_2$)$_{n1}$;

n, n2, n3, n4, n5 are equal to 0, n1 is 1 and the —(CH$_2$)$_{n1}$— group is bound to the phenyl ring through the [C]$_2$ or [C]$_3$ or [C]$_4$;

or n, n2, n5 are 1, n3 and n4 are equal to 0, and n1 is an integer from 1 to 10, Y$^1$ is —(CH$_2$)$_{na}$—CH=CH— wherein na is 0, X$_1$ is —WC(O)— wherein W is oxygen and the WC(O) group is bound to the phenyl ring through the [C]$_4$, R$^4$ is CH$_3$ and the (OR$^4$) group is bound to the phenyl ring through the [C]$_3$;

d)

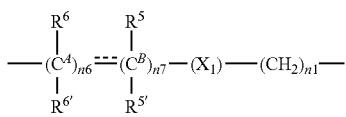
(V)

wherein n1 is an integer from 1 to 10;

X$_1$ is —WC(O)— wherein W is sulfur;

n6 is 1 n7 is 1,

R$^5$, R$^{5'}$ and R$^{6'}$ are H, R$^6$ is, NHCOCH$_3$ and the —ONO$_2$ is bound to the —(CH$_2$)$_{n1}$— group;

e)

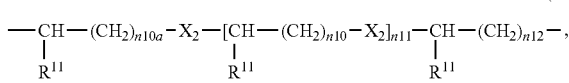
(VI)

wherein

X$_2$ is O or S, and n11 is 0, n10a is an integer from 0 to 10, n12 is an integer from 1 to 10, R$^{11}$ is H or a nitrooxy group and the —ONO$_2$ group is bound to (CH$_2$)$_{n12}$;

Another group of preferred compounds comprises compounds of formula (I)

wherein s is 1,

A is a β-adrenergic blocker residues of formula (II) as above defined,

Z$_1$ is H,

Z is —(CO)— or —C(O)O— and

Y is a bivalent radical having the following meanings:

c)

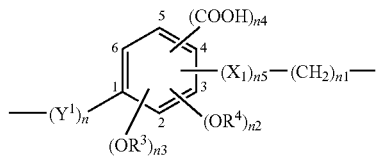
(IV)

wherein the —ONO$_2$ group is bound to (CH$_2$)$_{n1}$;

n, n2, n3, n4, n5 are equal to 0, n1 is 1 and the —(CH$_2$)$_{n1}$— group is bound to the phenyl ring through the [C]$_2$ or [C]$_3$ or [C]$_4$;

or in formula (IV)

n, n2, n5 are 1, n3 and n4 are equal to 0, n1 is an integer from 1 to 10,

Y$^1$ is —(CH$_2$)$_{na}$—CH=CH— wherein na is 0, X$_1$ is —WC(O)— wherein W is oxygen and the WC(O) group is bound to the phenyl ring through the [C]$_4$, R$^4$ is CH$_3$ and the (OR$^4$) group is bound to the phenyl ring through the [C]$_3$;

Another groups of preferred compounds comprises compounds of formula (I) wherein:

s is 1,

A is the β-adrenergic blocker residues of formula (II) wherein

R$_1$ is

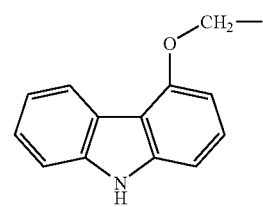
(IIb)

R$_2$ is

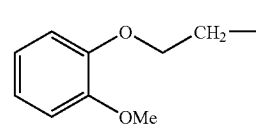
(IIIa)

Z$_1$ is H and Z is —(CO)— or —C(O)O— and

Y is a bivalent radical having the following meanings:

a) straight C$_1$-C$_{10}$ alkylene, preferably C$_3$-C$_6$ alkylene;

c)

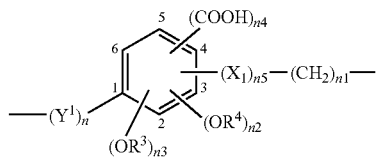
(IV)

wherein the —ONO$_2$ group is bound to (CH$_2$)$_{n1}$;

n, n2, n3, n4, n5 are equal to 0, n1 is 1 and the —(CH$_2$)$_{n1}$— group is bound to the phenyl ring through the [C]$_2$ or [C]$_3$ or [C]$_4$;

or in formula (IV)
n, n2, n5 are 1, n3 and n4 are equal to 0,
n1 is an integer from 1 to 10,
$Y^1$ is —$(CH_2)_{na}$—CH=CH— wherein na is 0,
$X_1$ is —WC(O)— wherein W is oxygen and the WC(O) group is bound to the phenyl ring through the $[C]_4$, $R^4$ is $CH_3$ and the $(OR^4)$ group is bound to the phenyl ring through the $[C]_3$;

d)

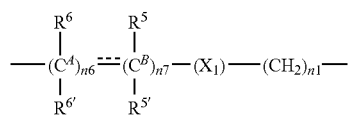

(V)

wherein
n1 is an integer from 1 to 10,
n6 and n7 are 1, $X_1$ is —WC(O)— wherein W is sulfur,
$R^5$, $R^{5'}$ and $R^{6'}$ are H, $R^6$ is $NHCOCH_3$ and the —$ONO_2$ is bound to the —$(CH_2)_{n1}$— group;

e)

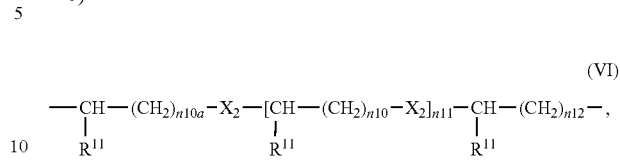

wherein
$X_2$ is O or S, and n11 is 0,
n10a is an integer from 0 to 10,
n12 is an integer from 1 to 10,
$R^{11}$ is H or a nitrooxy group
and the —$ONO_2$ group is bound to $(CH_2)_{n12}$.

Most preferred compounds of formula (I) according to the present invention are the following:

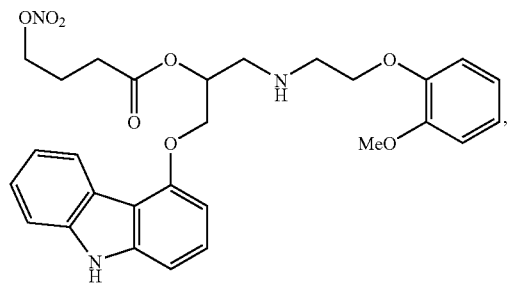

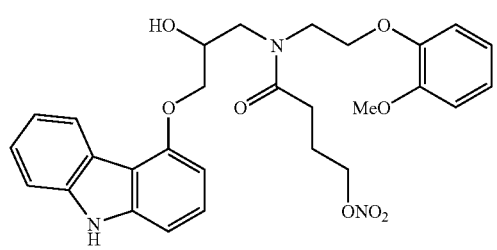

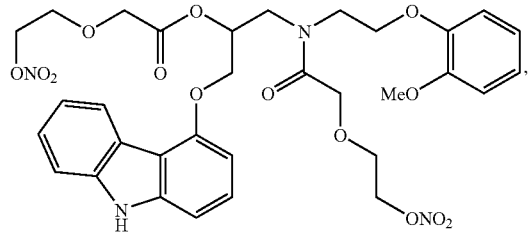

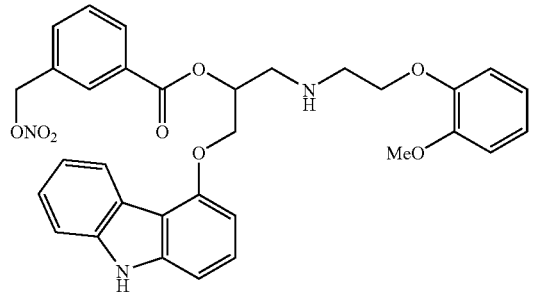

(9)
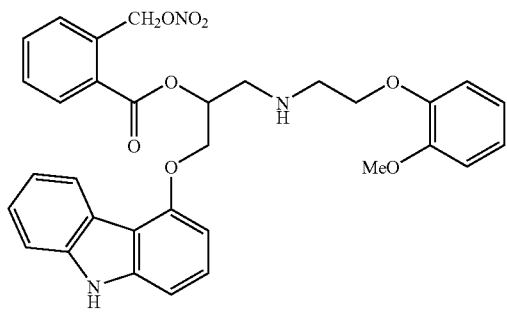
(10)
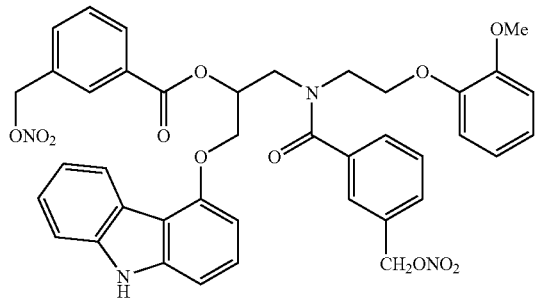
(11)
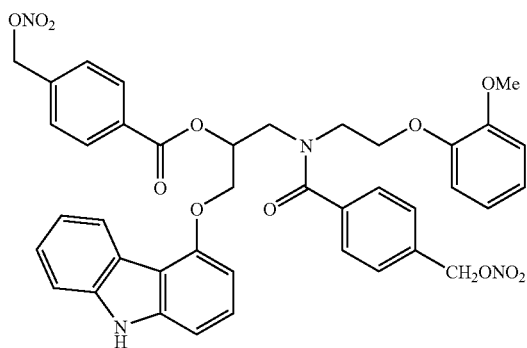
(12)
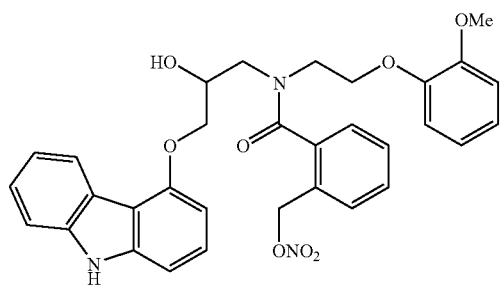
(13)
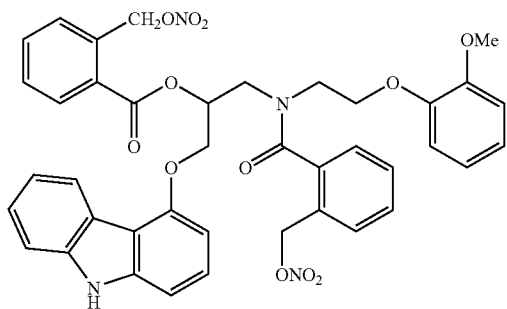
(14)
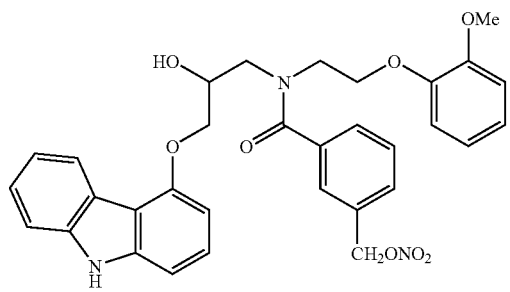
(15)
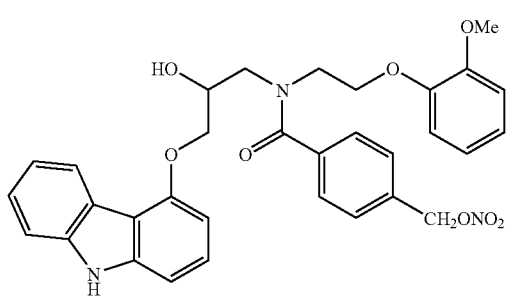

-continued
(16)
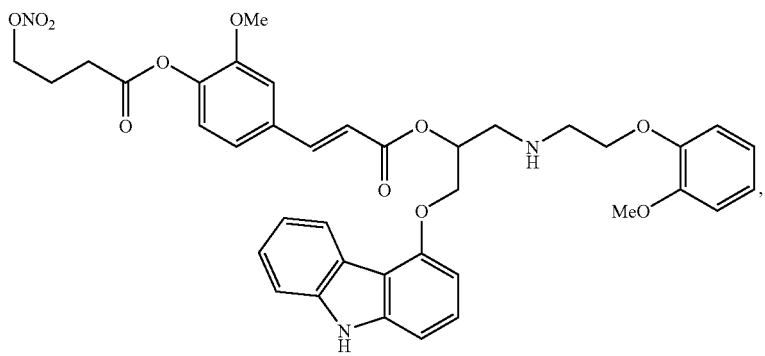
(17)
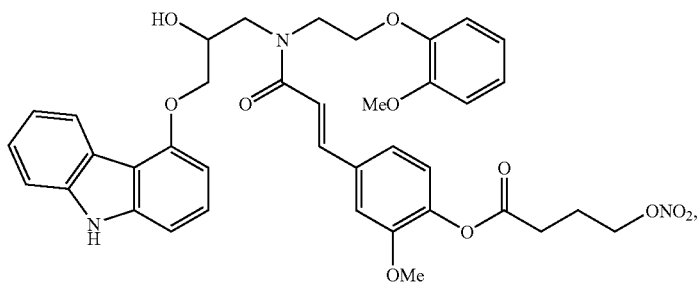
(18)
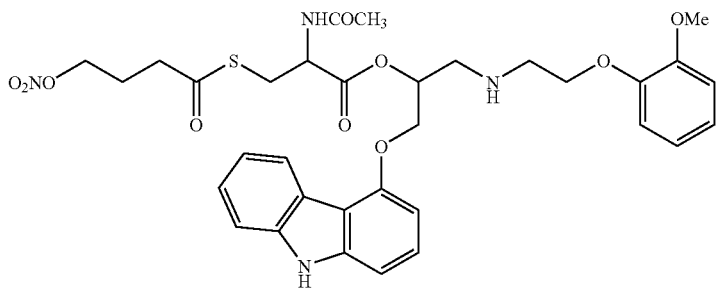
(19)
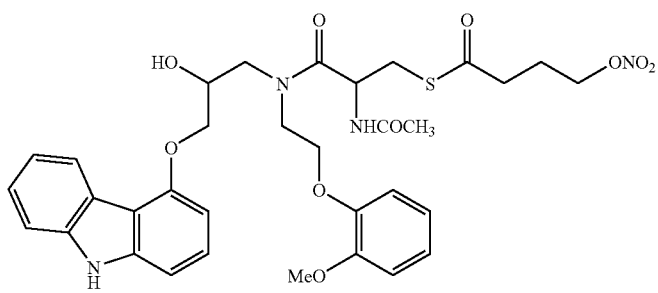
(20)
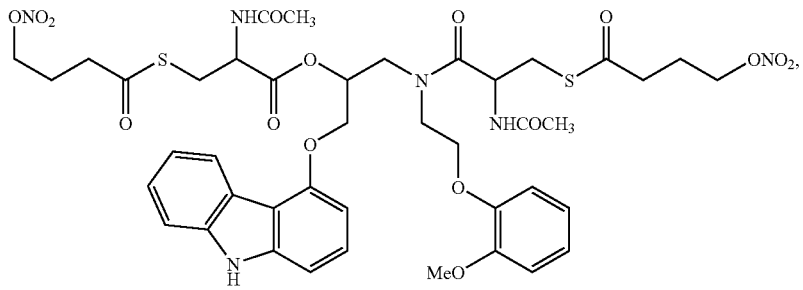

-continued
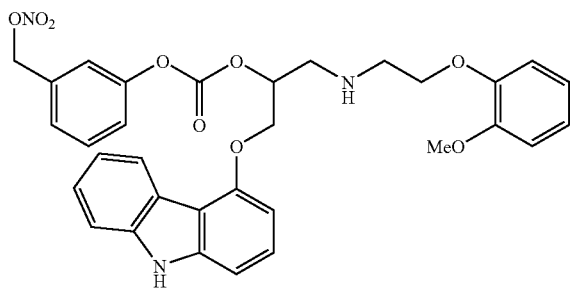
(21)
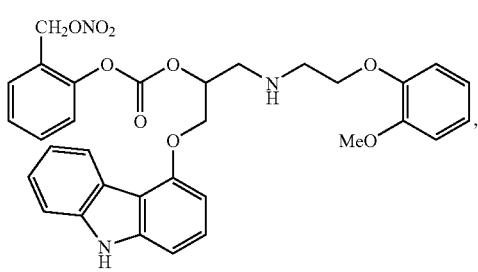
(22)
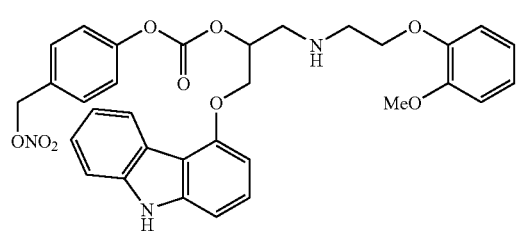
(23)
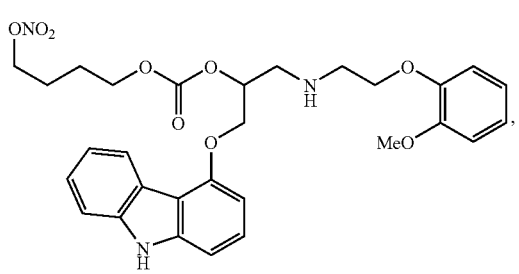
(24)
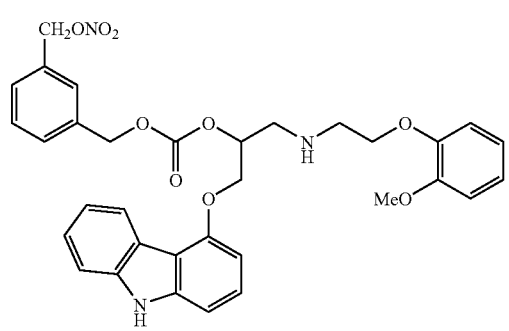
(25)
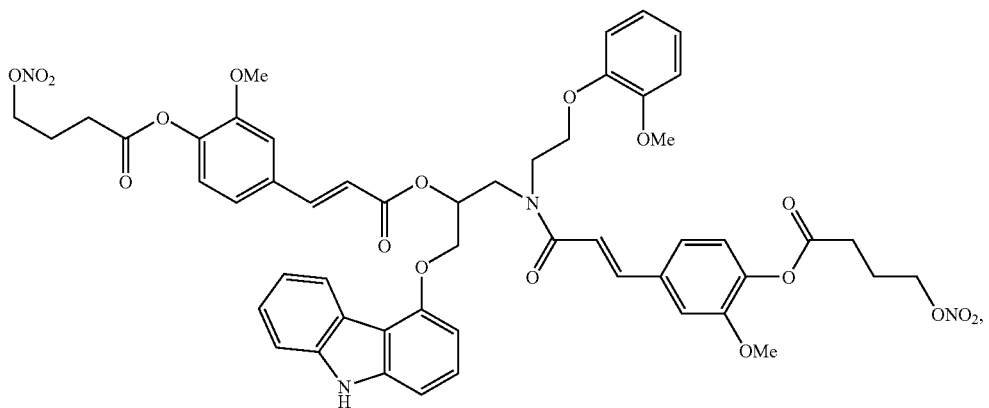
(26)
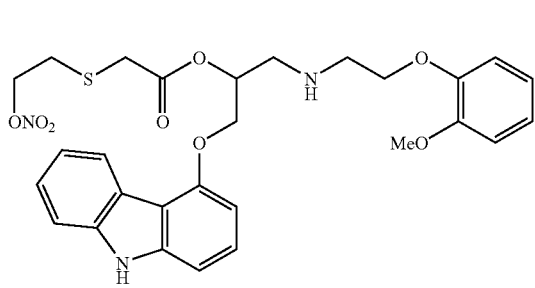
(27)
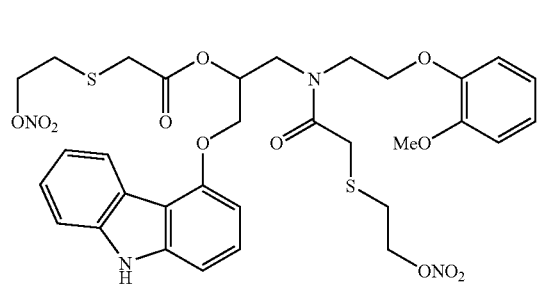
(28)

-continued
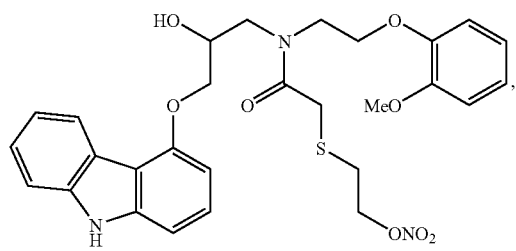 (29)
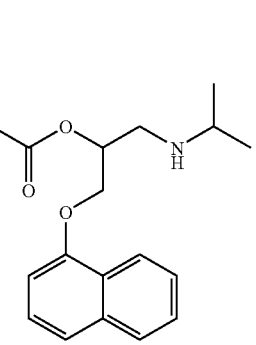 (30)
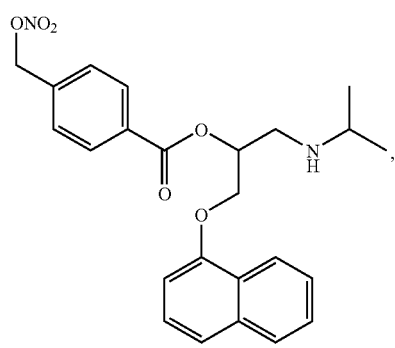 (31)
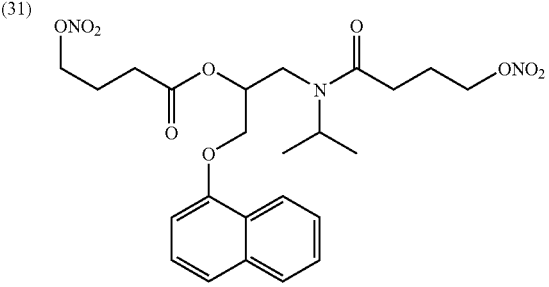 (33)
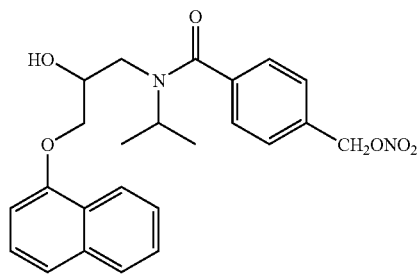 (34)
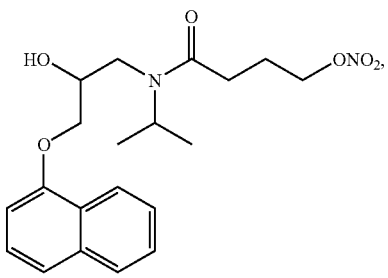 (35)
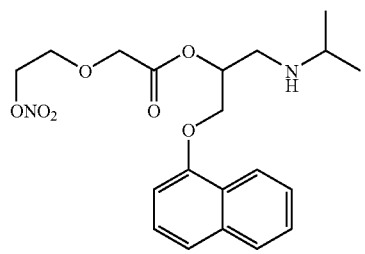 (36)
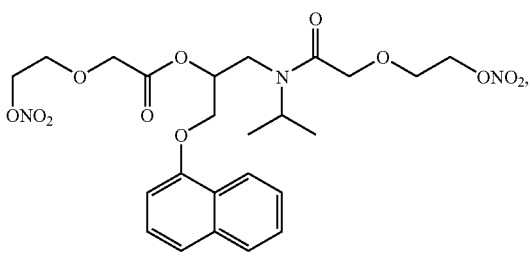 (37)
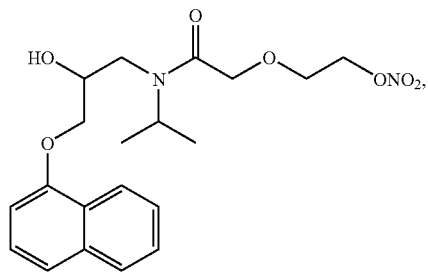 (38)
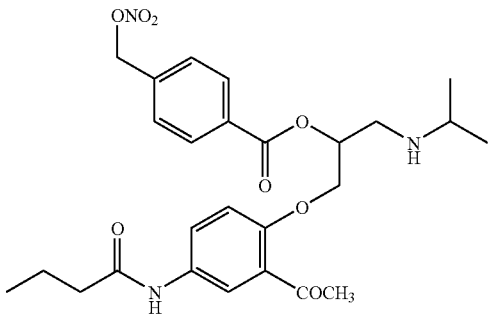 (39)

(40)
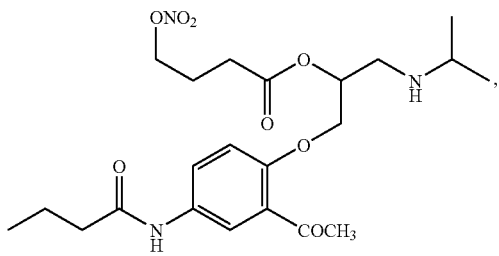
(41)
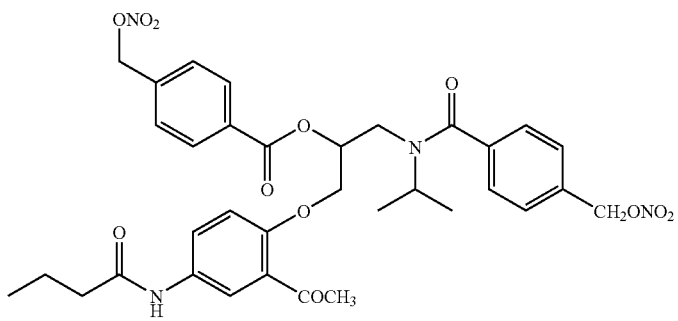
(42)
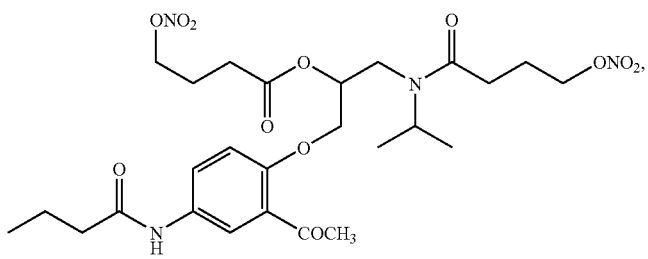
(43)
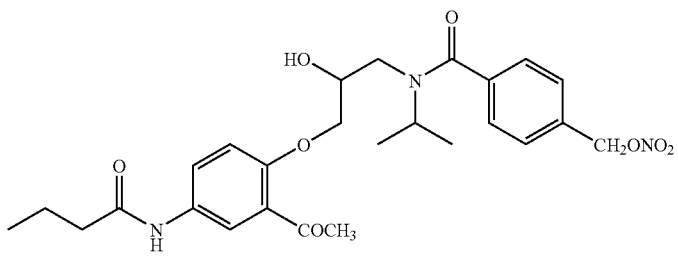
(44)
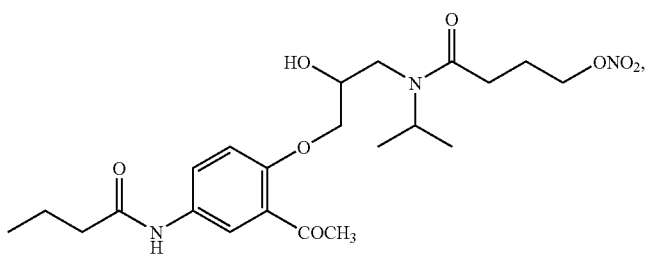
(45)
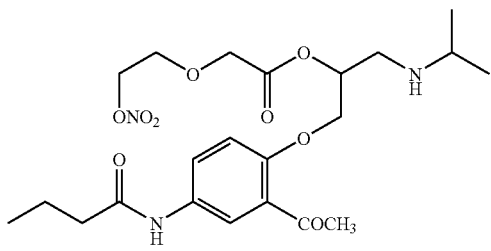

-continued
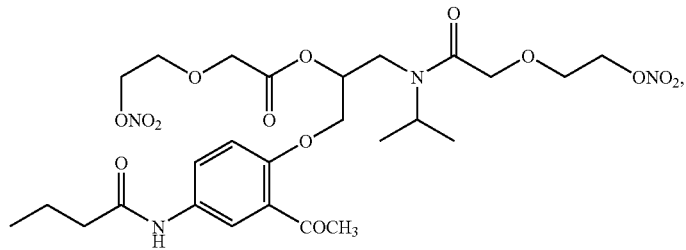
(46)
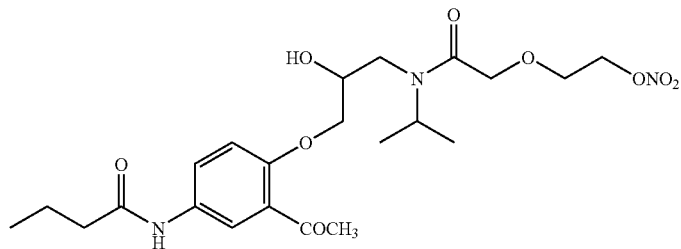
(47)
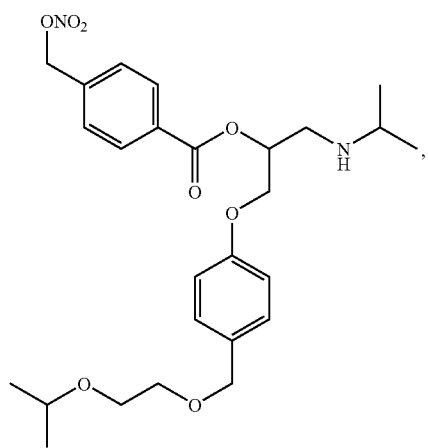
(48)
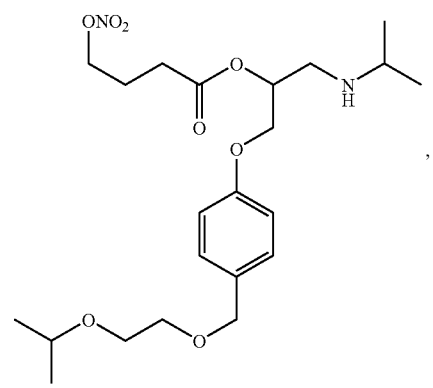
(49)
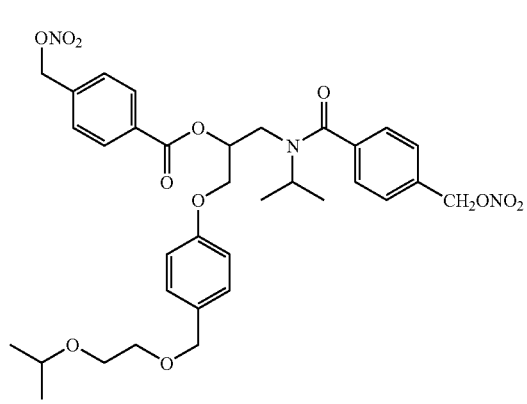
(50)
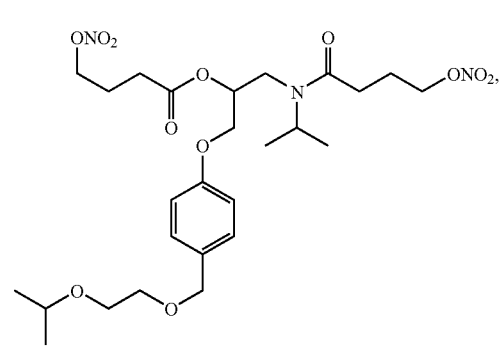
(51)

(52)
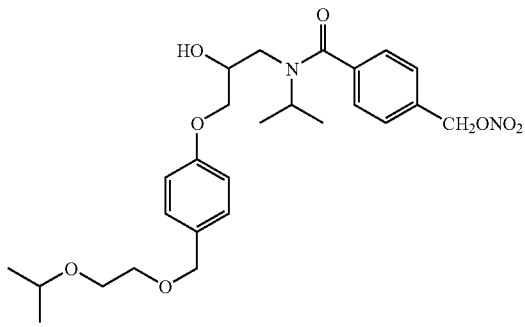
(53)
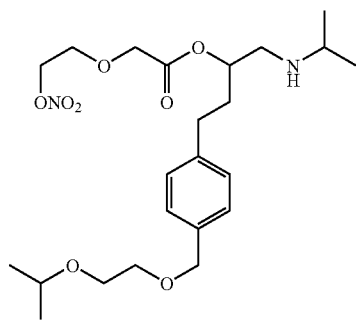
(54)
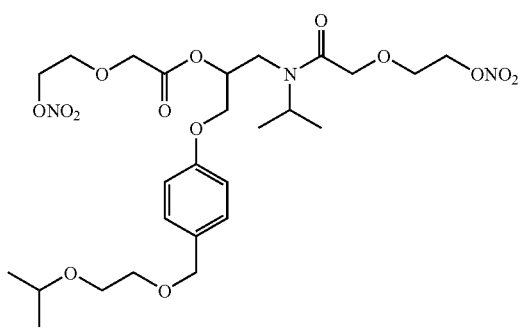
(55)
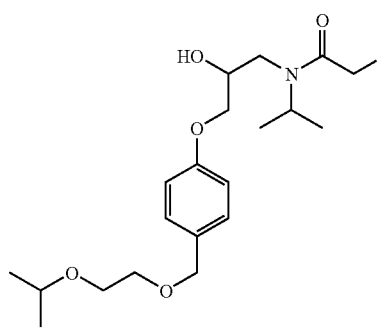
(56)
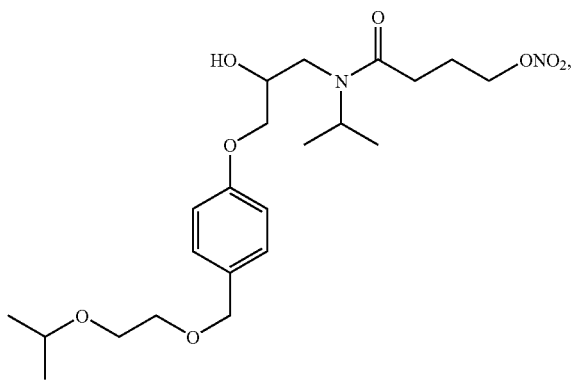
(57)
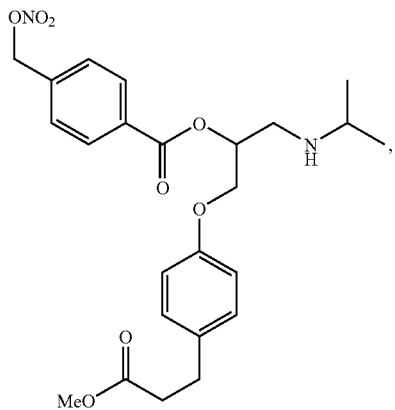
(58)
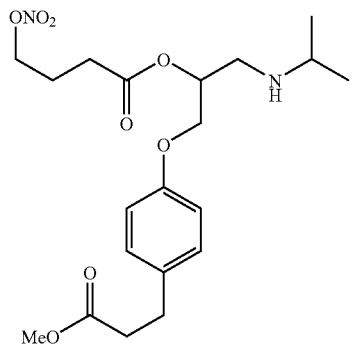

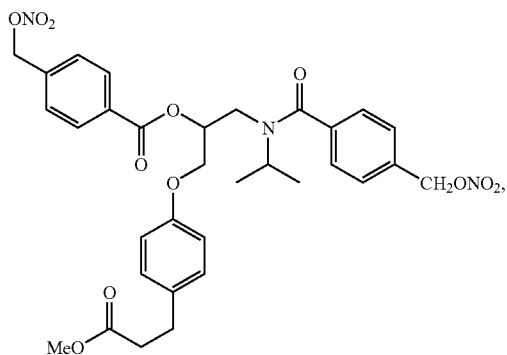
(59)
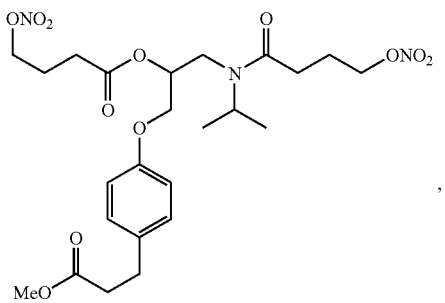
(60)
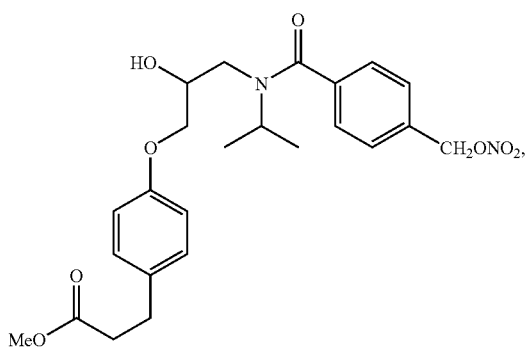
(61)
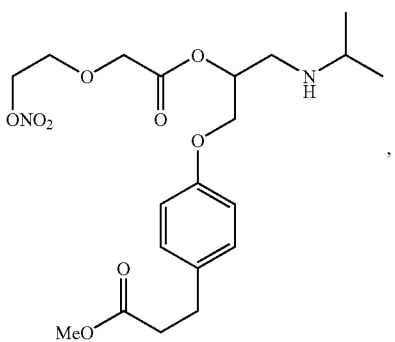
(62)
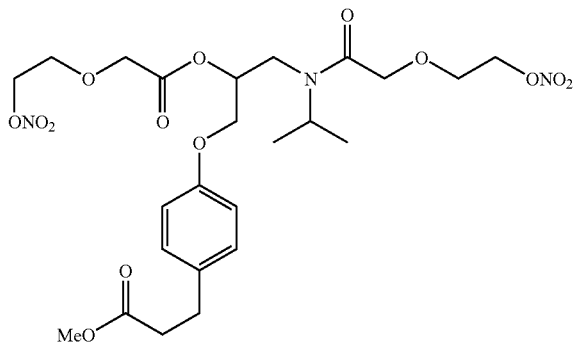
(63)
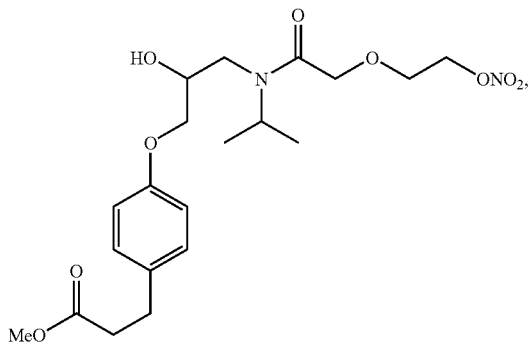
(64)
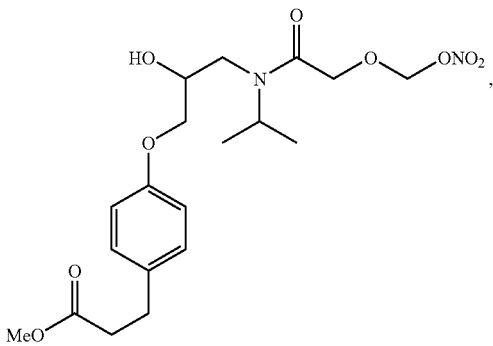
(65)

-continued
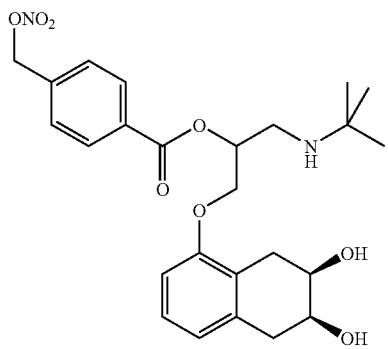
(66)
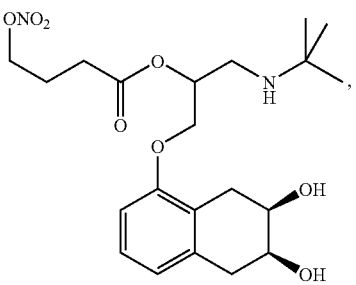
(67)
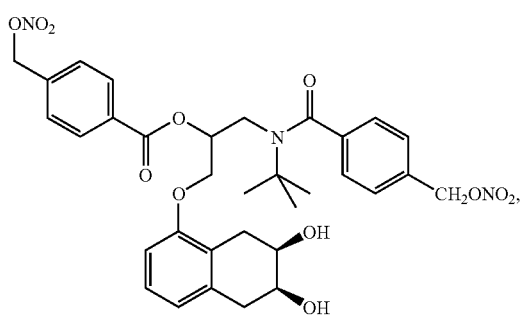
(68)
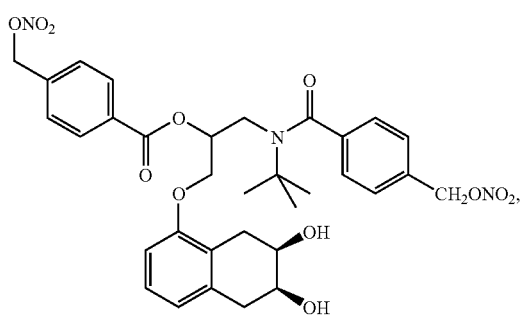
(69)
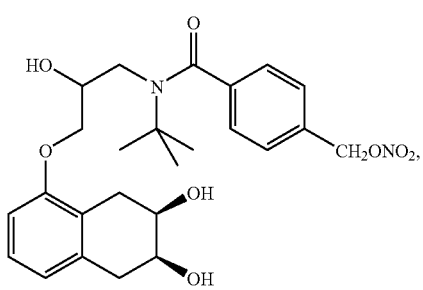
(70)
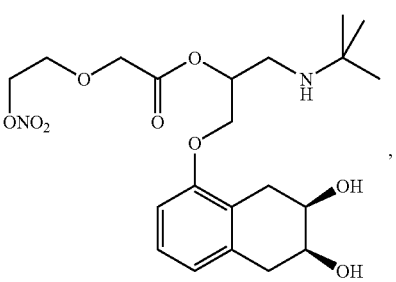
(71)
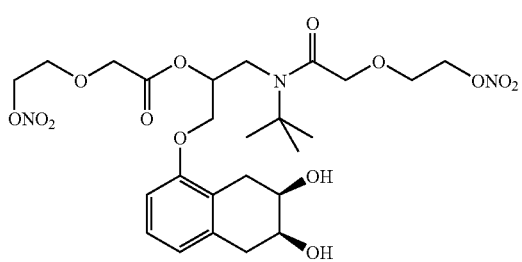
(72)
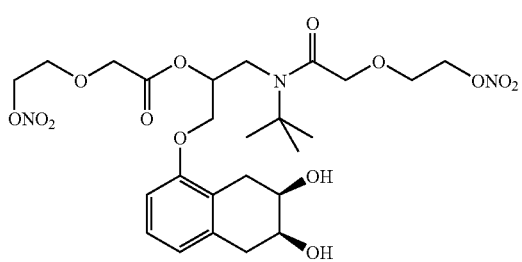
(73)
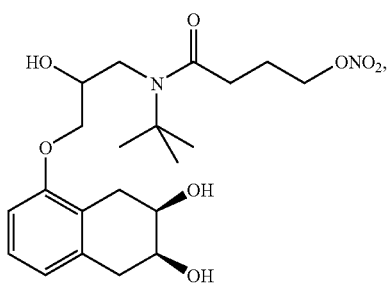
(74)
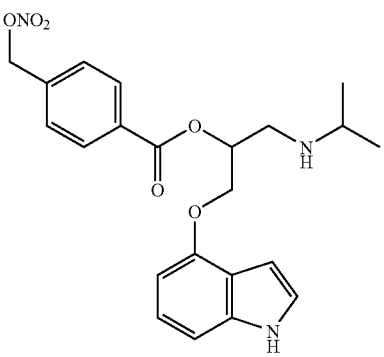
(75)

-continued
(76)
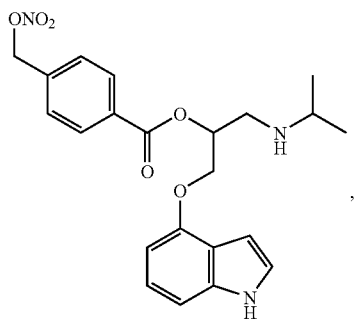
(77)
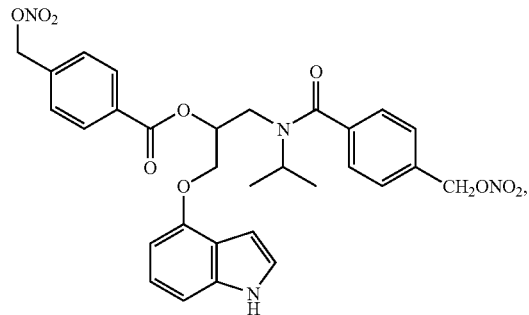
(78)
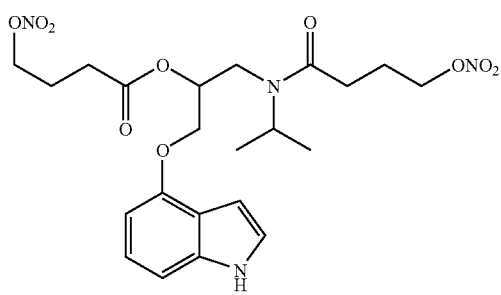
(79)
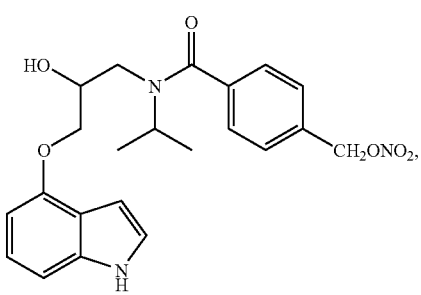
(80)
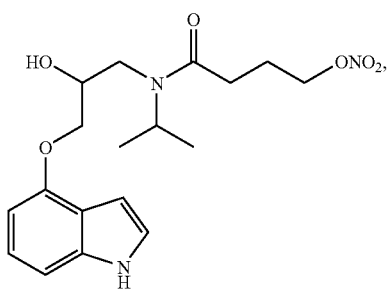
(81)
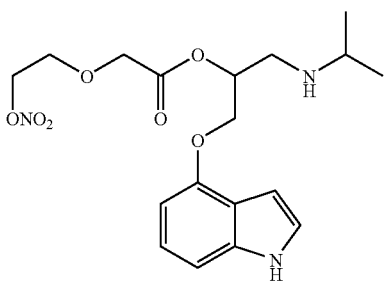
(82)
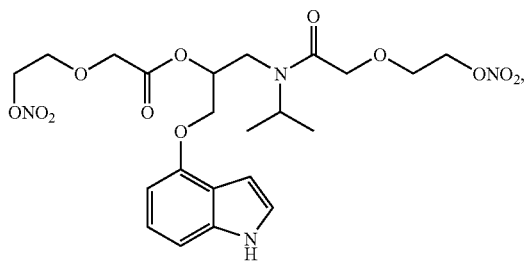
(83)
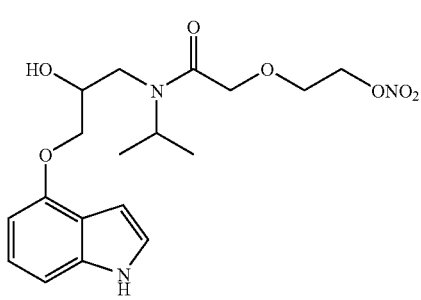
(84)
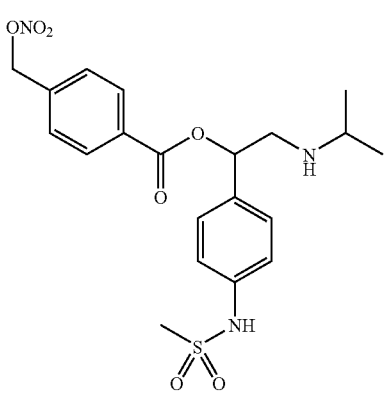

-continued
(85)
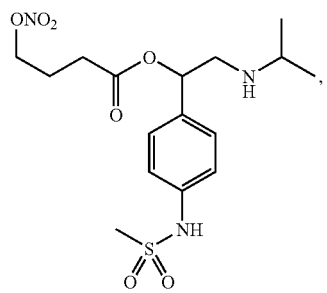
(86)
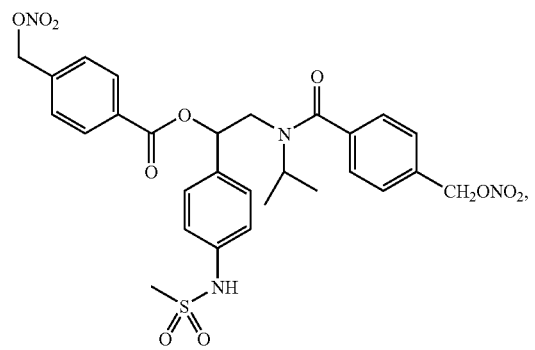
(87)
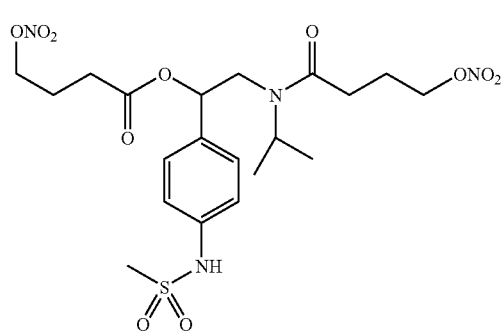
(88)
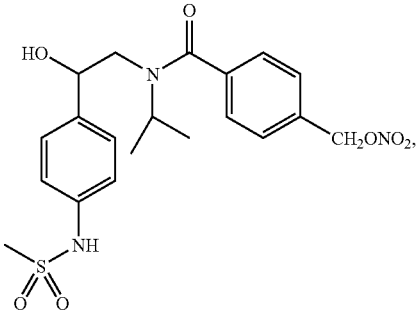
(89)
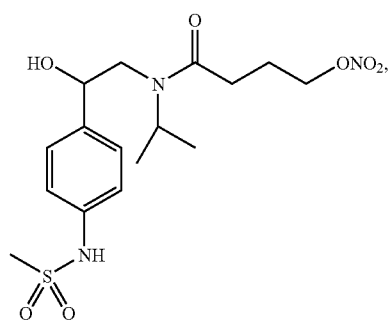
(90)
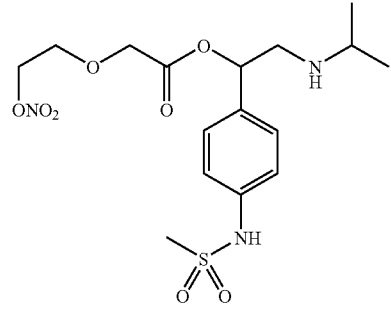
(91)
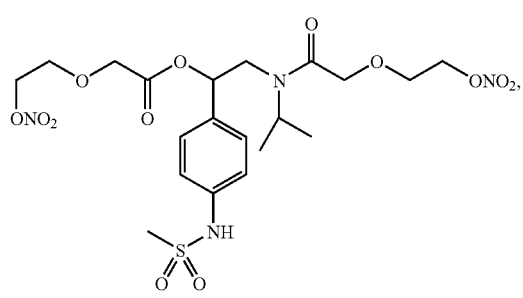
(92)
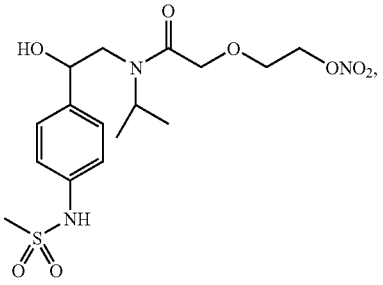
(93)
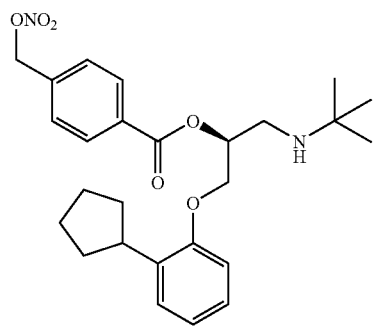
(94)
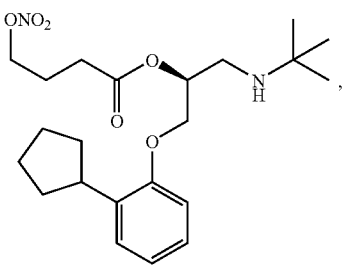

-continued
(95)
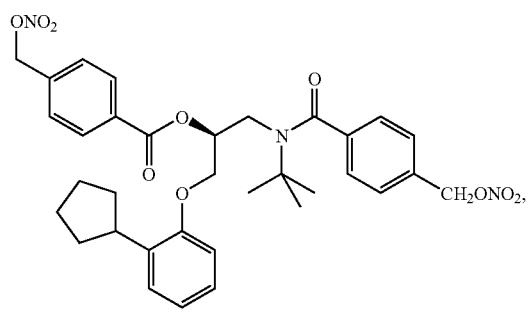
(96)
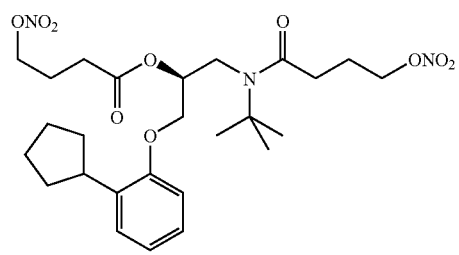
(97)
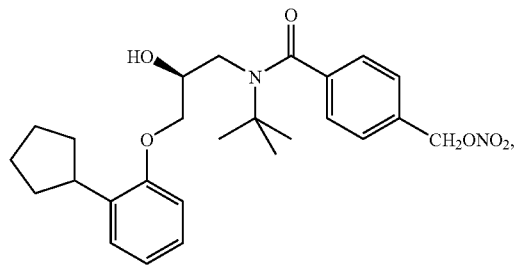
(98)
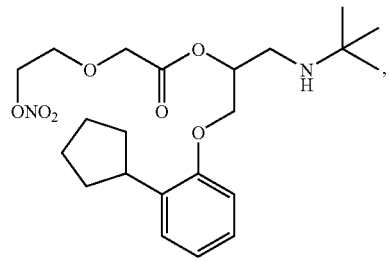
(99)
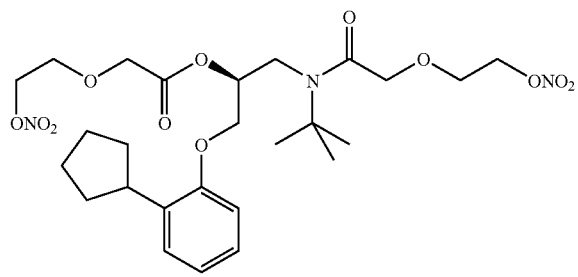
(100)
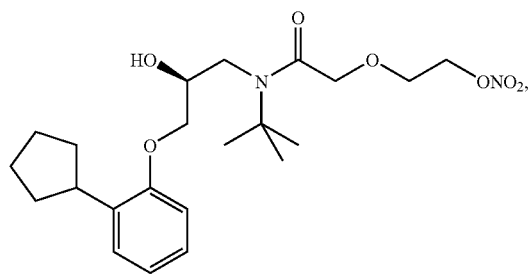
(101)
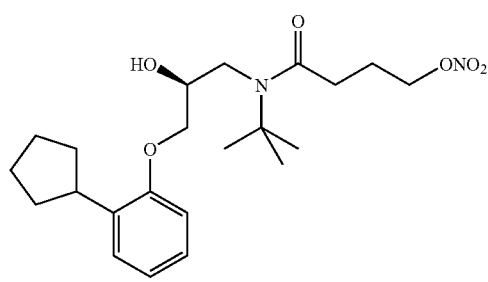
(102)
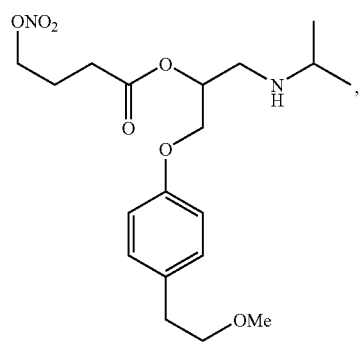

-continued
(103)
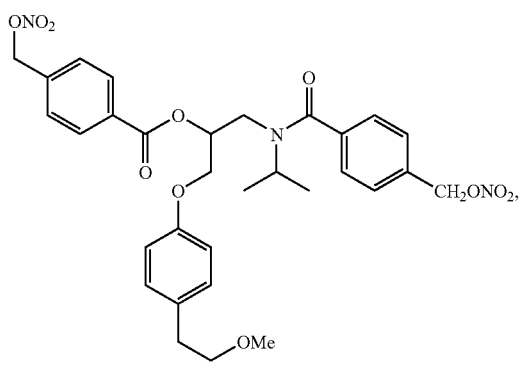
(104)
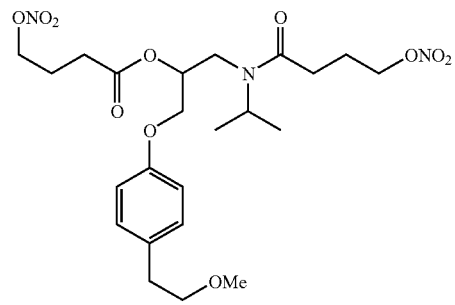
(105)
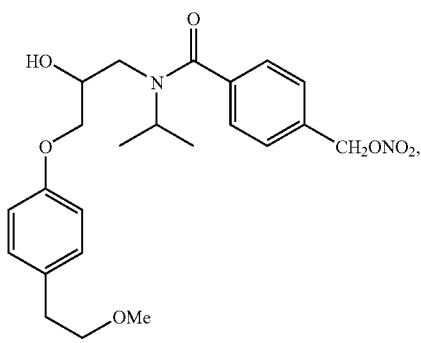
(106)
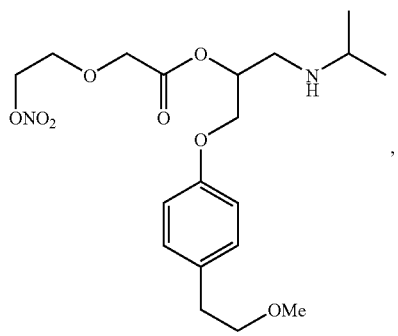
(107)
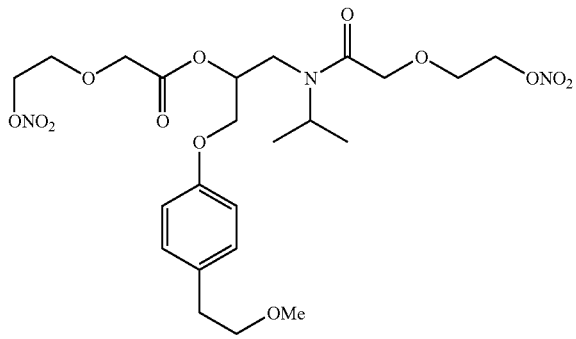
(108)
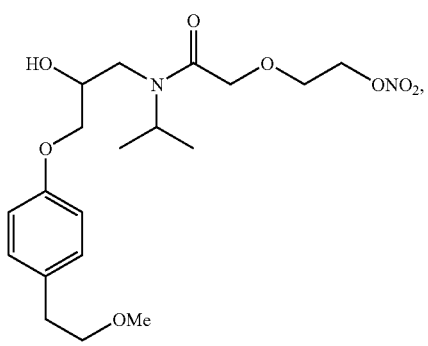
(109)
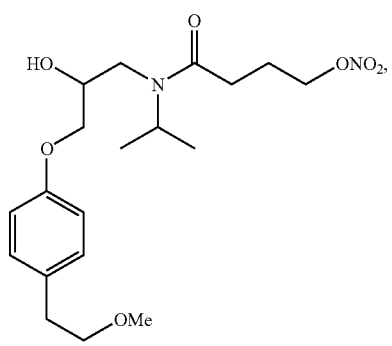

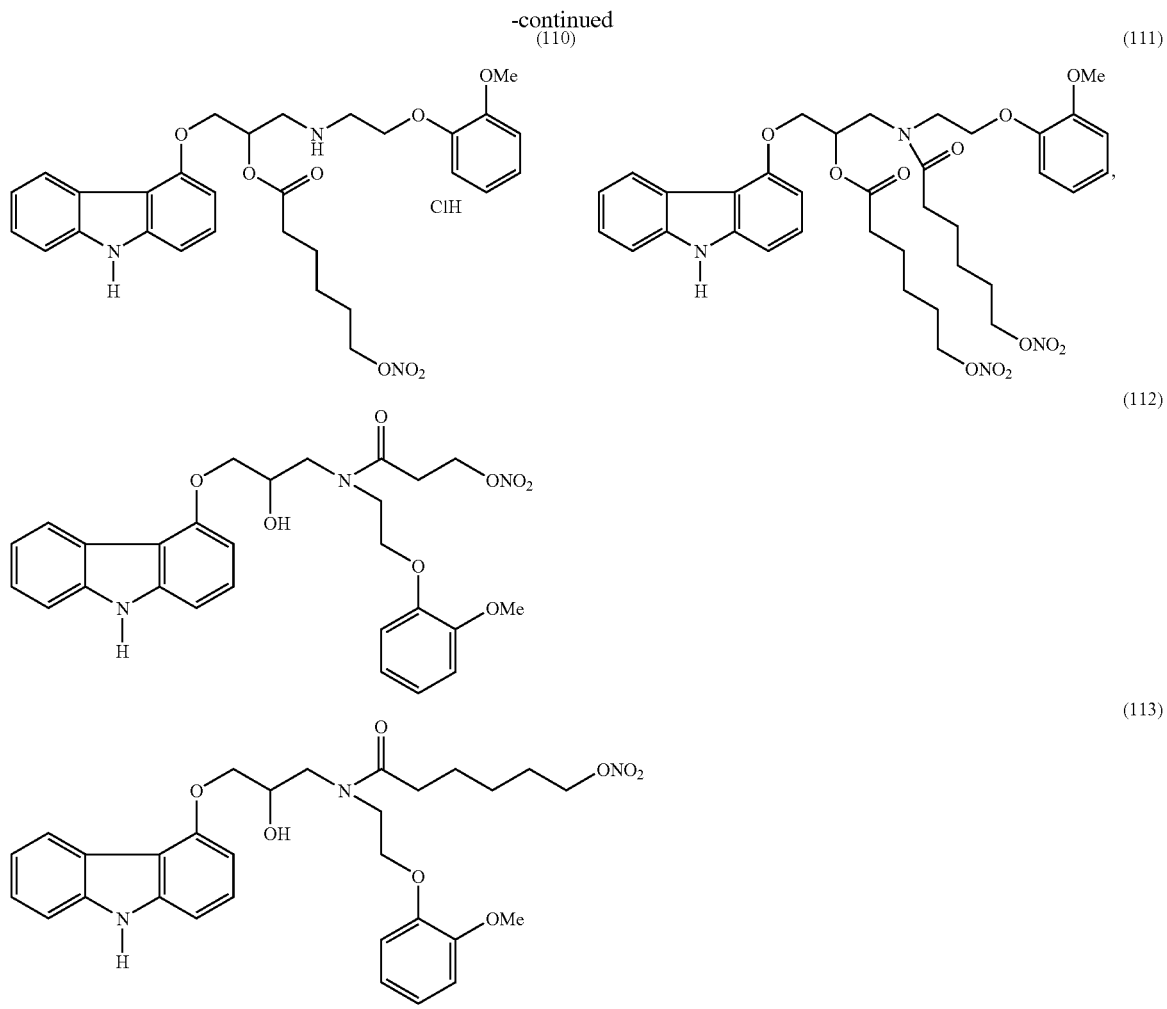

Examples of "straight or branched $C_1$-$C_{20}$ alkylene" include, but are not limited to, methylene, ethylene, propylene, isopropylene, n-butylene, pentylene, n-hexylene and the like.

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of pharmaceutical acceptable organic acids are: oxalic, tartaric, maleic, succinic, citric acids. Examples of pharmaceutical acceptable inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

The compounds and compositions of the present invention can be administered by any available and effective delivery system including but not limited to, orally, bucally, parenterally, by inhalation spray, by topical application, by injection, transdermally, or rectally (e.g. by the use of suppositories) in dosage unit formulations containing conventional nontoxic pharmaceutically acceptable carriers, adjuvants, and vehicles. Parenteral includes subcutaneous injections, intravenous, intramuscular, intrasternal injection, or infusion technique.

Solid dosage forms for oral administration can include for example capsule, tablets, pills, powders, granules and gel. In such solid dosage forms, the active compounds can be admixed with at least one inert diluent such as sucrose, lactose or starch. Such dosage form can also comprise, as normal practice, additional substance other than inert diluent, e.g., lubricating agent such as magnesium stearate.

Injectable preparations, for example sterile injectable aqueous or oleaginous suspensions can be formulated according to the known art using suitable dispersing agents, wetting agents and/or suspending agents.

The composition of this invention can further include conventional excipients, i.e., pharmaceutical acceptable organic or inorganic substances which do not deleteriously react with the active compounds.

The doses of β-adrenergic blockers nitrooxyderivatives can be determinated by standard clinique technique and are in the same ranges or less than as described for commercially available compounds as reported in the: Physician's Desk Reference, Medical Economics Company, Inc., Oradell, N. J., 58th Ed., 2004; The pharmacological basis of therapeutics, Goodman and Gilman, J. G. Hardman, L. e. Limbird, 20th Ed.

EXPERIMENTAL

Synthesis Procedure

Compounds of the invention can be synthesized as shown in Schemes 1 to 6. Compounds of general formula (I) A-(Y—ONO$_2$)$_s$, defined in Scheme 1-3 as compounds of formula D, wherein s is 1, Y is as above defined and A is a 0-adrenergic blocker residue of formula (II), wherein Z is —C(O)— and Z$_1$ is H, the enantiomers, diastereoisomer and a pharmaceutically acceptable salt thereof, can be prepared as outlined in Schemes 1-3.

are those described in T. W. Greene "Protective groups in organic synthesis", Harvard University Press, 1980.

The compounds of formula (H) wherein R$_1$, R$_2$, Z, P$_1$ and Y are as above defined, are converted to the esters of formula (i) wherein R$_1$, R$_2$, Y, Z, X$_3$ and P$_1$ are as above defined, by reaction with an appropriate acid (Q1) of formula X$_3$—Y—COOH wherein Y and X$_3$ are as above defined. The reaction is generally carried out in an inert organic solvent such as N,N'-dimethylformamide, tetrahydrofuran, benzene, toluene, dioxane, a polyhalogenated aliphatic hydrocarbon at a temperature from 0° C. to 50° C. in presence of a dehydrating agent such as dycyclohexylcarbodiimide DCC or 1-ethyl-3-(3-dimethylaminopropyl) carbodiimide hydrochloride (EDAC HCl) with a catalyst, such as 4-N,N-dimethylaminopyridine (DMAP).

The compounds of formula (H) wherein R$_1$, R$_2$ and P$_1$ are as above defined, can be obtained by deprotecting the hydroxylic group of the compounds of formula (G) wherein R$_1$, R$_2$ are as above defined and P is a hydroxylic protecting group such as silyl ethers, such as trimethylsilyl or tert-butyldimethylsilyl and those described in T. W. Greene "Protective

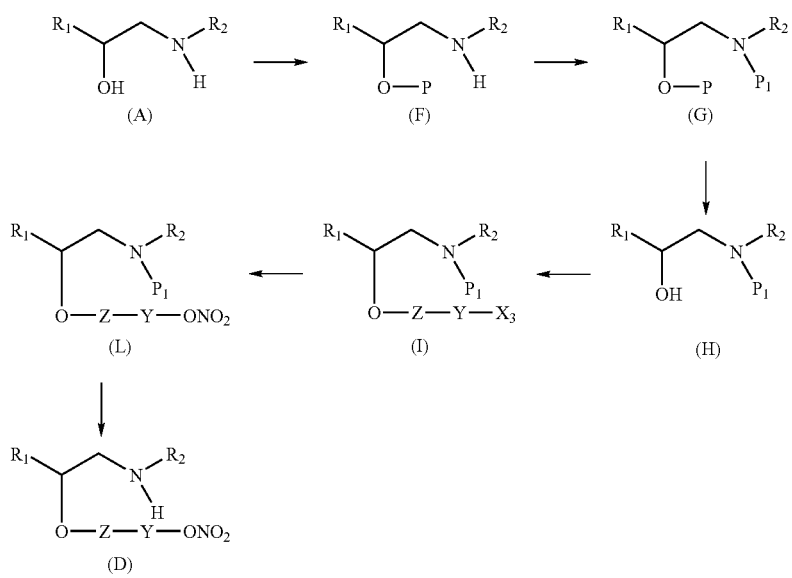

Scheme 1

Compounds of formula (i) wherein R$_1$, R$_2$, Z and Y are as above defined, P$_1$ is an amine protecting group such as tert-butyloxycarbonyl ester (t-Boc) and X$_3$ is an halogen atom preferably Cl, Br and I, are converted to compounds of formula (L) wherein R$_1$, R$_2$, P$_1$, Z and Y are as above defined, by reaction with AgNO$_3$ in a suitable organic solvent such as acetonitrile, tetrahydrofurane, a silver nitrate molar excess is preferably used and the reaction is carried out, in the dark, at a temperature from room temperature to the boiling temperature of the solvent. The compounds of formula (L) are converted to the compounds of formula (D) by deprotecting the amine group (strong acid, such as HCl in dioxane or trifluoroacetic acid, is used to remove a t-butyl carbamate). Other preferred methods for removing the amine protecting groups groups in organic synthesis", Harvard University Press, 1980. Fluoride ion is the preferred method for removing silyl ether protecting group.

The compounds of formula (G) wherein R$_1$, R$_2$, P and P$_1$ are as above defined, can be obtained by reacting the compounds of formula (F) wherein R$_1$, R$_2$ and P are as above defined with a suitable amine protecting group (P$_1$) as above described.

The alcohol group of the compounds of formula (A) wherein R$_1$, R$_2$ are as above defined, is protected to afford the compounds of formula (F) wherein R$_1$, R$_2$ are as above defined Preferred protecting group for the alcohol moiety are silyl ethers, such as trimethylsilyl or tert-butyl-dimethylsilyl.

The compounds (A) wherein $R_1$, $R_2$ are as above defined are commercially available, the acids of formula $X_3$—Y—COOH wherein $X_3$ is as above defined, are commercially available.

Scheme 2

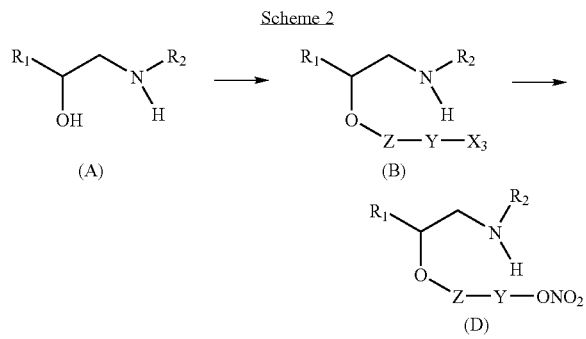

Compounds of formula (B) wherein $R_1$, $R_2$, Z, Y are as above defined and $X_3$ is an halogen atom, such as Cl, Br and I, are converted to compounds of formula (D) wherein $R_1$, $R_2$, Z and Y are as above defined, by reaction with $AgNO_3$ in a suitable organic solvent such as acetonitrile, tetrahydrofurane, a silver nitrate molar excess is preferably used and the reaction is carried out, in the dark, at a temperature from room temperature and the boiling temperature of the solvent.

The compounds of formula (B) wherein $R_1$, $R_2$, Z, Y and $X_3$ are as above defined can be obtained by reaction of the compounds of formula (A) with an appropriate acyl chloride (Q) of formula $X_3$—Y—C(O)Cl, wherein $X_3$ is chosen among chlorine, bromine, and Y is as above defined. The esterification is carried out in an inert organic solvent such as N,N'-dimethylformamide, tetrahydrofuran, benzene, toluene, chloroform in presence of a base as triethylamine, pyridine at a temperature from room temperature and 50° C. The reaction is completed within a time range from 30 minutes to 24 hours.

Alternatively the compounds of formula (B) can be obtained by reaction of compounds of formula (A) with an acid (Q1) of formula $X_3$—Y—C(O)OH in the presence of a dehydrating agent as dicyclohexylcarbodiimide (DCC) or N'-(3-dimethylaminopropyl)-N-ethylcarbodiimide hydrochloride (EDAC) and a catalyst, such as N,N-dimethylamino pyridine. The reaction is carried out in an inert organic solvent such as as N,N'-dimethylformamide, tetrahydrofuran, benzene, toluene, dioxane, a polyhalogenated aliphatic hydrocarbon at a temperature from 0° C. and 50° C. The reaction is completed within a time range from 30 minutes to 36 hours.

The compounds of formula (Q1), where $X_3$ is an halogen atom are commercially available or can be obtained from the corresponding commercially available hydroxy acid by well known reactions, for example by reaction with thionyl or oxalyl chloride, halides of $P^{III}$ or $P^V$ in solvents inert such as toluene, chloroform, DMF, etc.

The compounds (A) wherein $R_1$, $R_2$ are as above defined are commercially available Scheme 3

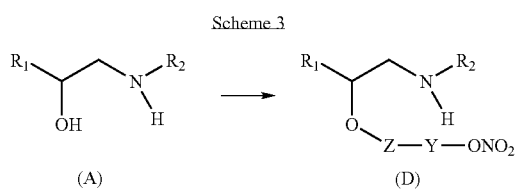

Alternatively the compounds of formula (D) can be obtained as described below. The compounds of formula are converted to the compounds (D) by reaction of hydroxy group with a nitrooxy derivative, containing activated acylating group, of formula Cl(O)C—Y—$ONO_2$.

The nitrooxy compounds can be obtained from the corresponding alcohols of formula Cl(O)C—Y—OH by reaction with nitric acid and acetic anhydride in a temperature range from −50° C. to 0° C. or from the corresponding halogen derivatives of formula Cl(O)C—Y-Hal by reaction with silver nitrate in the presence of an inert solvent such as acetonitrile, tetrahydrofurane. A silver nitrate molar excess is preferably used and the reaction is carried out, in the dark, a temperature from the boiling temperature and room temperature. The reaction is completed within a time range from 30 minutes to 3 days.

The compounds of general formula (I) A-(Y—$ONO_2$)$_s$, defined in Scheme 4 as compounds of formula (D1), wherein s is 1, Y is as above defined and A is a β-adrenergic blocker residue of formula (II), wherein Z is —C(O)O— and $Z_1$ is H, the enantiomers, diastereoisomer and a pharmaceutically acceptable salt thereof, can be prepared as outlined in Scheme 4.

Scheme 4

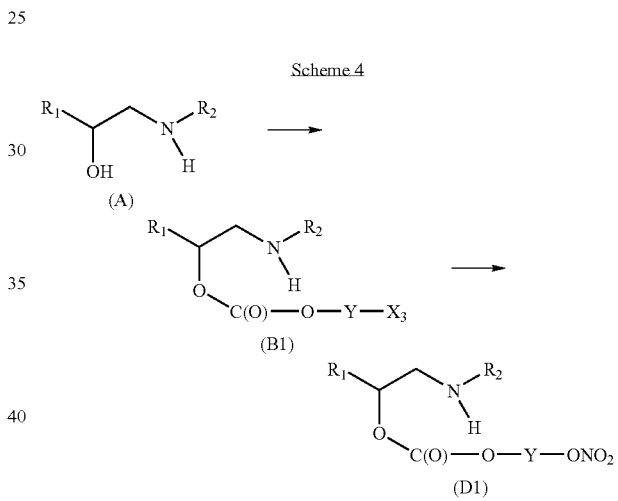

The compounds of formula (B1) wherein $R_1$, $R_2$, Y are as above defined and $X_3$ is an halogen atom, such as Cl, Br and I, are converted to compounds of formula (D1) wherein $R_1$, $R_2$, and Y are as above defined, by reaction with $AgNO_3$ in a suitable organic solvent such as acetonitrile, tetrahydrofurane, a silver nitrate molar excess is preferably used and the reaction is carried out, in the dark, at a temperature from room temperature and the boiling temperature of the solvent.

The compounds of formula (A) wherein $R_1$ and $R_2$ are as above defined are converted to the compounds (B1) by reaction with an appropriate compound (Q2) having formula $X_3$—Y—OC(O)Cl wherein $X_3$ is Cl, Br or I, and Y is as defined above. The reaction is generally carried out in presence of a base in an aprotic polar or non-polar solvent such as THF or $CH_2Cl_2$ at temperature range between 0°-65° C. or in a double phase system $H_2O/Et_2O$ at temperature range between 20°-40° C.

The compounds of formula (Q2) are commercially available or can be obtained from the corresponding alcohols by reaction with triphosgene in presence of an organic base.

The compounds of general formula (I) A-(Y—$ONO_2$)$_s$, defined in Scheme 5 as compounds of formula (D), wherein s is 1, Y is as above defined and A is a β-adrenergic blocker residue of formula (II), wherein Z is

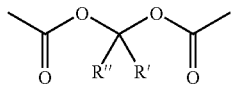

wherein R' and R" are H or straight or branched $C_1$-$C_4$ alkyl and $Z_1$ is H, the enantiomers, diastereoisomer and a pharmaceutically acceptable salts thereof, may be prepared as outlined in Scheme 5:

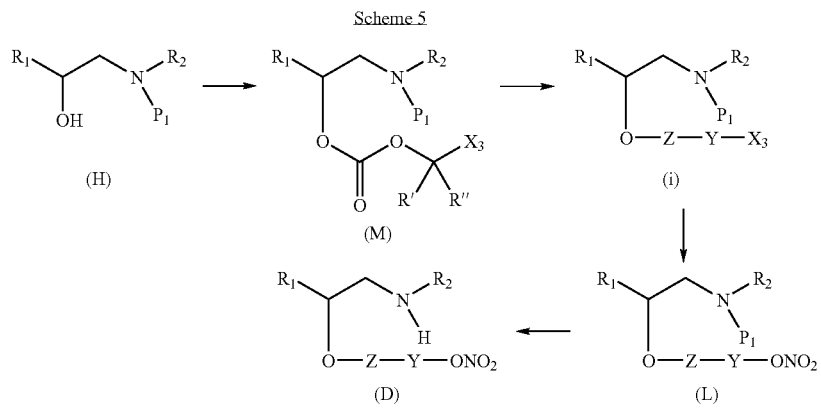

The compounds of formula (i) wherein $R_1$, $R_2$, Z and Y are as above defined, $P_1$ is an amine protecting group such as tert-butyloxycarbonyl ester (t-Boc) and $X_3$ is an halogen atom such as Cl, Br and I, are converted to compounds of formula (L) wherein $R_1$, $R_2$, $P_1$, Z and Y are as above defined, by reaction with $AgNO_3$ in a suitable organic solvent such as acetonitrile, tetrahydrofurane, a silver nitrate molar excess is preferably used and the reaction is carried out, in the dark, at a temperature from room temperature and the boiling temperature of the solvent. The compounds of formula (L) are converted to the compounds of formula (D) by deprotecting the amine group (strong acid, such as HCl in dioxane or trifluoroacetic acid, is used to remove a t-butyl carbamate). Other preferred methods for removing the amine protecting groups are those described in T. W. Greene "Protective groups in organic synthesis", Harvard University Press, 1980.

The compounds of formula (i) wherein $R_1$, $R_2$, Y, $X_3$, Z and $P_1$ are as above defined, can be obtained by reacting the compounds of formula (M) wherein $R_1$, $R_2$, $P_1$, R', R" and $X_3$ are as above defined, with an acid (Q1) of formula $X_3$—Y—COOH wherein $X_3$ is an halogen atom and Y is as above defined. The reaction is carried out in an inert organic solvent such as N,N'-dimethylformamide, tetrahydrofuran, benzene, toluene, dioxane, a polyhalogenated aliphatic hydrocarbon at a temperature range from 0° C. and 50° C. in the presence of a dehydrating agent such as dycyclohexylcarbodiimide DCC or 1-ethyl-3-(3-dimethylaminopropyl)carbodiimide hydrochloride (EDAC HCl) with a catalyst, such as 4-N,N-dimethylaminopyridine (DMAP).

The reaction is complete within a time ranges from 30 minutes to 24 hours.

The compounds of formula (M) wherein $R_1$, $R_2$, $P_1$, R', R" and $X_3$ are as above defined, can be obtained by reacting the compounds the of formula (H) with a compound (S) of formula $X_3$—C(R')(R")—OC(O)$X_3$ wherein $X_3$ is an halogen atom. The reaction is carried out in presence of an organic or inorganic base in a polar solvent as DMF, THF, acetonitrile at a temperature in the range from −5° C. to 60° C. or in a double phase system according to methods well known in the literature.

The amine group of the compounds (A) is protected to afford the compounds of formula (H) wherein $P_1$ is a suitable amine protecting group such as tert-butyloxycarbonyl ester (t-Boc) The compounds (S) are commercially available.

The compounds of general formula (I) A-(Y—$ONO_2$)$_s$, defined in Scheme 6 as compounds of formula (E), wherein s is 2, Y is as above defined and A is a β-adrenergic blocker residue of formula (II), wherein $Z_1$ and Z are —C(O)—, the enantiomers, diastereoisomer and a pharmaceutically acceptable salt thereof, can be synthesized as shown in Scheme 6.

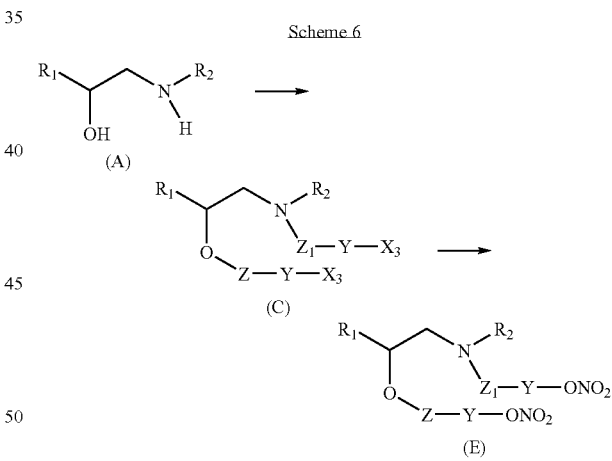

Compounds of formula (C) wherein $R_1$, $R_2$, Z, $Z_1$ and Y are as above defined and $X_3$ is an halogen atom, such as Cl, Br and I, are converted to compounds of formula (E) wherein $R_1$, $R_2$, Z and Y are as above defined, by reaction with $AgNO_3$ in a suitable organic solvent such as acetonitrile, tetrahydrofurane, a silver nitrate molar excess is preferably used and the reaction is carried out, in the dark, at a temperature from room temperature and the boiling temperature of the solvent.

The compounds of formula (C) wherein $R_1$, $R_2$, Z, $Z_1$, Y and $X_3$ are as above defined can be obtained by reaction of the compounds of formula (A) with an appropriate acyl halide (Q) of formula $X_3$—Y—C(O)Cl, wherein $X_3$ is chosen among chlorine, bromine, and Y is as above defined. The reaction is carried out in an inert organic solvent such as N,N'-dimethylformamide, tetrahydrofuran, benzene, toluene, chloroform in presence of a base as triethylamine, pyridine at a temperature from room temperature and 50° C. The reaction is completed within a time range from 30 minutes to 24 hours.

Alternatively the compounds of formula (C) can be obtained by reaction of the compounds of formula (A) with an acid (Q1) of formula $X_3$—Y—COOH in the presence of a dehydrating agent such as dicyclohexylcarbodiimide (DCC) or N'-(3-dimethylaminopropyl)-N-ethylcarbodiimide hydrochloride (EDAC) and a catalytic amount of N,N-dimethylamino pyridine. The reaction is carried out in an inert organic solvent such as N,N'-dimethylformamide, tetrahydrofuran, benzene, toluene, dioxane, a polyhalogenated aliphatic hydrocarbon at a temperature from 0° C. and 50° C. The reaction is completed within a time range from 30 minutes to 36 hours.

The compounds of formula (Q1), where $X_3$ is an halogen atom are commercially available or can be obtained from the corresponding commercially available hydroxy acid by well known reactions, for example by reaction with thionyl or oxalyl chloride, halides of $P^{III}$ or $P^V$ in solvents inert such as toluene, chloroform, DMF, etc.

The compounds (A) wherein $R_1$, $R_2$ are as above defined are commercially available.

The compounds of formula (E) can also be obtained as described below. The compounds of formula A are converted to the compounds (E) by reaction with a nitrooxy derivative of formula Cl(O)C—Y—ONO$_2$ containing an activated acylating group.

The nitrooxycompounds can be obtained from the corresponding alcohols of formula Cl(O)C—Y—OH by reaction with nitric acid and acetic anhydride in a temperature range from −50° C. to 0° C. or from the corresponding halogen derivatives of formula Cl(O)C—Y-Hal by reaction with silver nitrate in the presence of an inert solvent such as acetonitrile, tetrahydrofurane. A silver nitrate molar excess is preferably used and the reaction is carried out, in the dark, a temperature from the boiling temperature and room temperature. The reaction is completed within a time range from 30 minutes to 3 days.

EXAMPLES

The following non-limiting examples further describe and enable one of ordinary skilled in the art to make and use the present invention.

Example 1

4-(Nitrooxymethyl)benzoic acid 1-(9H-carbazol-4-yloxy)-3-[[2-(2-methoxyphenoxy)ethyl]amino]-2-propanoate of formula (8)

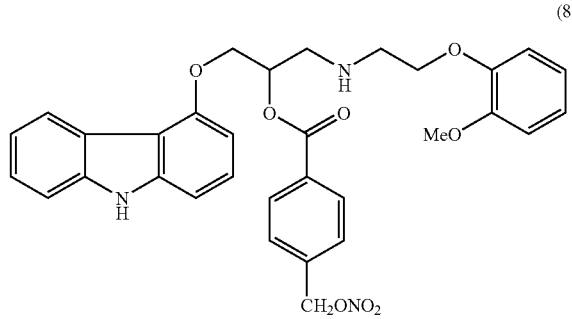

(8)

1a. 4-(Chloromethyl)benzoic acid 1-(9H-carbazol-4-yloxy)-3-[[2-(2-methoxyphenoxy)ethyl]amino]-2-propanoate To a solution of carvedilol (2 g, 5 mmol) in chloroform (50 ml) 4-chloromethyl benzoic acid (0.9 g, 5.5 mmol), EDAC (1.15 g, 6 mmol) and N,N-dimethylaminopyridine (catalytic amount) were added. The reaction was stirred at room temperature for 24 hours. The solution was treated with water and the organic layer was dried over sodium sulphate. The solvent was evaporated and the residue was purified by flash chromatography eluting with n-hexane/ethyl acetate 6/4 (Rf=0.2). The title product 0.27 g was obtained as a white powder.

1b. 4-(Nitrooxymethyl)benzoic acid 1-(9H-carbazol-4-yloxy)-3-[[2-(2-methoxyphenoxy)ethyl]amino]-2-propanoate A solution of the product of Example 1a (0.27 g, 0.48 mmol) and silver nitrate (0.16 g, 0.96 mmol) in acetonitrile (30 ml) was stirred at 60° C., in the dark, for 36 hours. The precipitated (silver salts) was filtered off and the solvent was evaporated under vacuum. The residue was treated with chloroform and water. The organic layer was dried over sodium sulphate. The solvent was evaporated and the residue was purified by flash chromatography eluting with ethyl acetate/n-hexane 6/4. The title product 0.03 g was obtained as a white powder.

$^1$H-NMR (DMSO) δ (ppm): 11.31 (1H,s); 8.15 (2H,m); 7.8-7.5 (2H,m); 7.43 (1H,d); 7.30 (2H,m); 7.15-6.85 (7H,m); 6.77 (1Hd); 6.03 (1H,m); 5.65 (2H,s); 4.55 (2H,m); 4.33 (2H,m); 4.0-3.7 (5H,m); 3.51 (2H,m).

Example 2

4-(Nitrooxymethyl)benzoic acid 1-(9H-carbazol-4-yloxy)-3-[[2-(2-methoxyphenoxy)ethyl][(4-nitrooxymethyl)benzoyl]amino]-2-propanoate of formula (11)

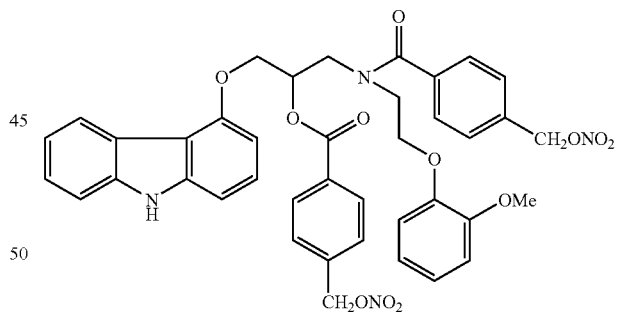

(11)

2a. 4-(Chloromethyl)benzoic acid 1-(9H-carbazol-4-yloxy)-3-[[2-(2-methoxyphenoxy)ethyl][(4-chloromethyl)benzoyl]amino]-2-propanoate To a solution of carvedilol (2 g, 5 mmol) in chloroform (50 ml) 4-chloromethyl benzoic acid (0.9 g, 5.5 mmol), EDAC (1.15 g, 6 mmol) and N,N-dimethylaminopyridine (catalytic amount) were added. The reaction was stirred for 24 hours at room temperature. The solution was treated with water and the organic layer was dried over sodium sulfate and filtered. The solvent was evaporated and the residue was purified by flash chromatography eluting with n-hexane/ethyl acetate 1/1 (Rf=0.42). The title product (0.06 g) was obtained as a white powder.

2b. 4-(Nitrooxymethyl)benzoic acid 1-(9H-carbazol-4-yloxy)-3-[[2-(2-methoxyphenoxy)ethyl][(4-nitrooxymethyl)benzoyl]amino]-2-propanoate A solution of the product of example 2a (0.06 g, 0.08 mmol) and silver nitrate (0.06 g, 0.32 mmol) in acetonitrile (20 ml) was stirred at 60° C., in the dark, for 36 hours. The precipitated (silver salts) was removed by filtration. The filtrate was concentrated and the residue was treated with chloroform and water. The combined organic layer extracts were dried over sodium sulfate and filtered. The solvent was evaporated and the residue was purified by flash chromatography eluting with n-hexane/ethyl acetate 6/4. The title product 0.015 g was obtained as a powder.

$^1$H-NMR (DMSO) δ (ppm): 1.24 (1H,s); 8.1 (3H,m); 7.7-7.2 (8H,m); 7.2-6.7 (8H,m); 6.05 (1H,m); 5.6-5.8 (4H,d); 4.55 (1H,m); 4.30 (2H,m); 4.15 (3H,m); 3.71 (5H,s).

Example 3

1-(9H-carbazolyloxy)-3-[[2-(2-methoxyphenoxy)ethyl][(4-nitrooxymethyl)benzoyl]amino]-2-propanol of formula (15)

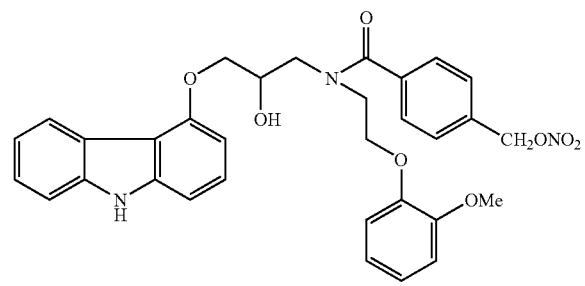

(15)

3a. 1-(9H-carbazol-4-yloxy)-3-[[2-(2-methoxyphenoxy)ethyl][(4-chloromethyl)benzoyl]amino]-2-propanol To a solution of carvedilol (2 g, 5 mmol) in chloroform (50 ml) 4-chloromethyl benzoic acid (0.9 g, 5.5 mmol), EDAC (1.15 g, 6 mmol) and N,N-dimethylaminopyridine (catalytic amount) were added. The reaction was stirred for 24 hours at room temperature. The solution was treated with water and the organic layer was dried over sodium sulfate and filtered. The solvent was evaporated and the residue was purified by flash chromatography eluting with n-hexane/ethyl acetate 6/4 (Rf=0.42). The title product 1.05 g was obtained as a white powder.

3b. 1-(9H-carbazol-4-yloxy)-3-[[2-(2-methoxyphenoxy)ethyl][(4-nitrooxymethyl)benzoyl]amino]-2-propanol A solution of the product of example 3a (1.0 g, 1.78 mmol) and silver nitrate (0.6 g, 3.6 mmol) in acetonitrile (100 ml) was stirred at 65° C., in the dark, for 32 hours. The precipitated (silver salts) was removed by filtration. The filtrate was concentrated and the residue was treated with methylene chloride and water. The combined organic layer extracts were dried over sodium sulphate. The solvent was evaporated and the residue was purified by flash chromatography eluting with n-hexane/ethyl acetate 1/1. The title product 0.4 g was obtained as yellow powder.

$^1$H-NMR (DMSO) δ (ppm): 11.24 (1H,s); 8.40-6.50 (15H, m); 5.61 (2H,m); 5.51 (1H,m); 5.36 (1H,m); 4.40-3.90 (4H, m); 3.74-3.71 (7H,m).

Example 4

1-(9H-carbazol-4-yloxy)-3-[[2-(2-methoxyphenoxy)ethyl][(3-nitrooxypropanoyl)amino]-2-propanol of formula (112)

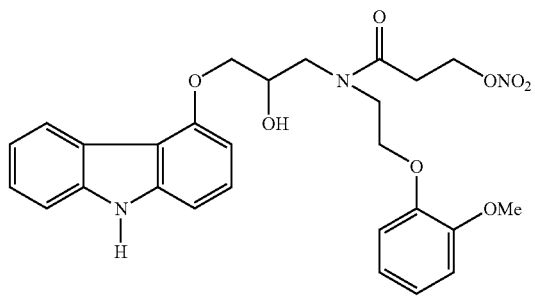

The compound was synthesized under the analogous procedure described in example 3 starting from carvedilol and 3-bromopropanoic acid.

$^1$H-NMR (DMSO) δ (ppm): 11.24 (1H, s); 8.25 (1H, dd); 7.46 (1H, dd); 7.29 (2H, m); 7.08 (2H, m); 6.90 (4H, m); 6.70 (1H, dd); 5.50 (1H, d); 4.80 (2H, m); 4.35 (1H, m); 4.20-3.6 (9H, m); 3.6-2.8 (4H, m).

Example 5

1-(9H-carbazol-4-yloxy)-3-[[2-(2-methoxyphenoxy)ethyl][(6-nitrooxyhexanoyl)amino]-2-propanol of formula (113)

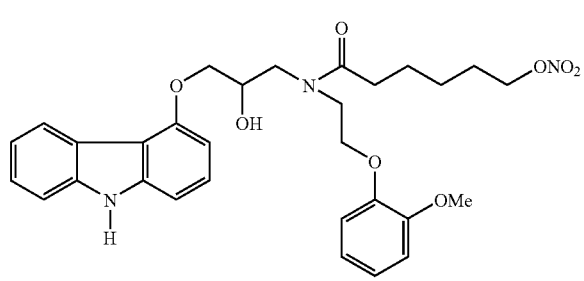

The compound was synthesized under the analogous procedure described in example 3 starting from carvedilol and 6-bromohexanoic acid.

$^1$H-NMR (DMSO) δ (ppm): 11.24 (1H, s); 8.25 (1H, dd); 7.46 (1H, dd); 7.29 (2H, m); 7.08 (2H, m); 6.90 (4H, m); 6.70 (1H, dd); 5.40 (1H, d); 4.50-3.50 (13H, m); 2.6-2.3 (2H, m); 1.70-0.50 (6H, m).

Example 6

6-(nitrooxy)hexanoic acid 1-(9H-carbazol-4-yloxy)-3-[[2-(2-methoxyphenoxy)ethyl]-[(6-nitrooxyhexanoyl]amino]-2-propanol of formula (111)

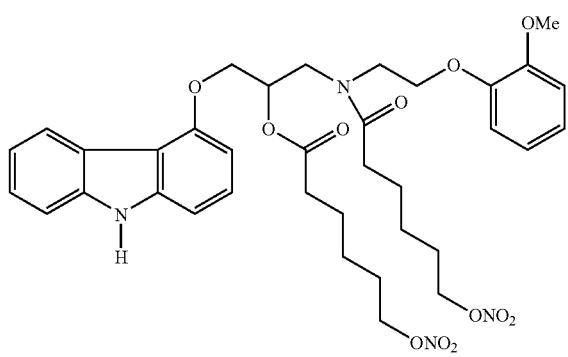

The compound was synthesized under the analogous procedure described in example 2 starting from carvedilol and 6-bromohexanoic acid.

$^1$H-NMR (DMSO) δ (ppm): 11.24 (1H, s); 8.15 (1H, dd); 7.46 (1H, dd); 7.29 (2H, m); 7.08 (2H, m); 6.90 (4H, m); 6.70 (1H, dd); 5.65 (1H, m); 4.6-4.20 (6H, m); 4.2-3.5 (9H, m); 2.50 (2H, m); 2.29 (2H, m); 1.70-0.60 (12H, m).

Example 7

6-(nitrooxy)hexanoic acid 1-(9H-carbazol-4-yloxy)-3-[[2-(2-methoxyphenoxy)ethyl]amino]-2-propanol hydrochloride of formula (110)

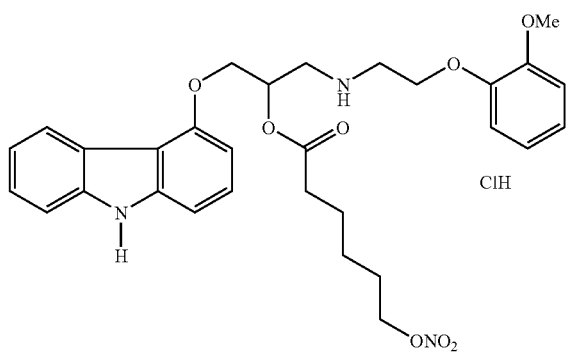

The compound was synthesized under the analogous procedure described in example 1 starting from carvedilol and 6-bromohexanoic acid.

$^1$H-NMR (DMSO) δ (ppm): 11.30 (1H, s); 8.15 (1H, dd); 7.44 (1H, dd); 7.32 (2H, m); 7.10-6.90 (6H, m); 6.70 (1H, dd); 5.65 (1H, m); 4.50-4.20 (7H, m); 3.90-3.40 (7H, m); 2.40 (2H, m); 1.60-1.10 (6H, m).

Example 8

Measurements of cGMP in Rat PC12 Cell Line cGMP contributes to the function and interaction of several vascular cell types and its dysfunction is involved in major cardiovascular diseases such as hypertension, diabetic complications, atherosclerosis, and tissue infarction. Therefore the extent of cGMP formation elicited by the compounds of the inventions was evaluated in the rat pheochromocytoma (PC12) cell line.

Tested Compounds
1) Carvedilol (parent drug)
2) 1-(9H-carbazol-4-yloxy)-3-[[2-(2-methoxyphenoxy)ethyl][(4-nitrooxymethyl)benzoyl]amino]-2-propanol (compound of example 3);
3) 4-(Nitrooxymethyl)benzoic acid 1-(9H-carbazol-4-yloxy)-3-[[2-(2-methoxyphenoxy)ethyl]amino]-2-propanoate (compound of example 1);
4) 1-(9H-carbazol-4-yloxy)-3-[[2-(2-methoxyphenoxy)ethyl][(3-nitrooxypropanoyl)amino]-2-propanol (compound of example 4);
5) 1-(9H-carbazol-4-yloxy)-3-[[2-(2-methoxyphenoxy)ethyl][(6-nitrooxyhexanoyl)amino]-2-propanol (compound of example 5).

Method

Cells were maintained at 37° C. in DMEM medium enriched with 10% horse serum and 5% foetal bovine serum under 5% $CO_2$ atmosphere. At the time of experiments the cells were washed once with Hank's Balanced Salt Solution (HBSS) supplemented with 0.05% ascorbic acid and preincubated in the same buffer for 10 min in a floating water bath. After the preincubation step, cells were exposed for additional 45 min to either control conditions or increasing concentrations of test compounds ranging from 0.1 to 25 μM, in the presence of the phosphodiesterase inhibitor, IBMX (100 μM) and the NO-independent activator of soluble guanylyl cyclase, YC-1 (20 μM). The reaction was terminated by the removal of the incubating buffer and consecutive addition of 100 μl of absolute ethanol. The organic extracts were then evaporated to dryness and the residues dissolved in aqueous buffer for quantitative determination of intracellular cGMP levels using the cGMP enzyme immunoassay kit.

The obtained results reported in Table 1 are expressed as $EC_{50}$ (μM) and efficacy Emax (% of vehicle). As shown in the table the nitroderivatives of carvedilol induced a consistent increase of intracellular cGMP formation in PC12 cell line. Conversely, this effect was not induced by the parent compound.

TABLE 1

Effects of the nitroxyderivatives of carvedilol and the carvedilol on cGMP accumulation in PC12 cells

| Compound | $EC_{50}$ (μM) | $E_{max}$ (% of vehicle) |
| --- | --- | --- |
| Carvedilol | Not effective | Not effective |
| Compound of example 3 | 1.8 | 565 |
| Compound of example 1 | 2.3 | 480 |
| Compound of example 4 | 1.7 | 395 |
| Compound of example 5 | 0.6 | 322 |

The invention claimed is:
1. A compound of general formula A-(Y—ONO$_2$)$_s$ (I) and the enantiomers, diastereoisomers and pharmaceutically acceptable salts thereof, wherein
s is an integer equal to 1;
A is selected from the following β-adrenergic blockers residues of formula (II):

(II)

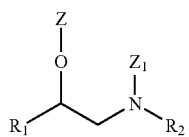

wherein
R₁ is

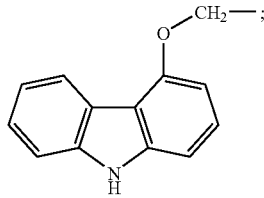
(IIb)

R₂ is

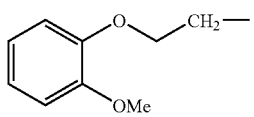
(IIIa)

Z is —C(O)—;
Z₁ is H;
Y is a bivalent radical selected from the group consisting of:
a)
    straight or branched $C_1$-$C_{20}$ alkylene being optionally substituted with one or more of the substituents selected from the group consisting of: halogen atoms, hydroxy, —ONO₂ or T, wherein T is —OC(O)($C_1$-$C_{10}$alkyl)-ONO₂, —O($C_1$-$C_{10}$alkyl)-ONO₂;
b)

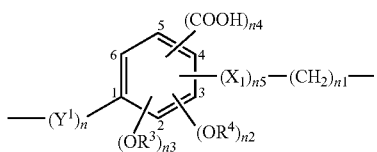
(IV)

wherein:
n is an integer from 0 to 20,
n1 is an integer from 1 to 20;
n2, n3, n4 and n5 are integers equal or different from each other, equal to 0 or 1,
$R^3$ and $R^4$ are independently selected from H or $CH_3$,
$Y^1$ is —CH₂— or —(CH₂)$_{na}$—CH=CH— wherein na is an integer from 0 to 20;
$X_1$ is —WC(O)— or —C(O)W—, wherein W is oxygen, sulfur or NH; and
c)

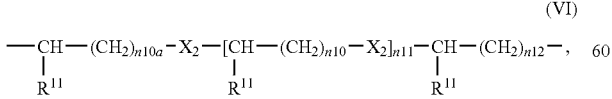
(VI)

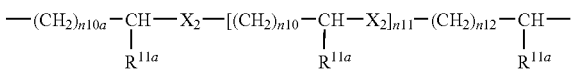
(VII)

wherein
$X_2$ is O or S,
n10a, n10 and n12 are integer independently selected from 0 to 20,
n11 is an integer from 0 to 6;
$R^{11}$ is H, $CH_3$ or nitrooxy group;
$R^{11a}$ is $CH_3$ or nitrooxy group;
and wherein (Y—ONO₂)$_s$ bonds with Z of formula (II).

2. A compound and the enantiomers, diastereoisomers and pharmaceutically acceptable salts thereof according to claim 1 wherein Y is a straight or branched $C_1$-$C_{10}$ alkylene.

3. A compound and the enantiomers, diastereoisomers and pharmaceutically acceptable salts thereof according to claim 1 wherein
Y is

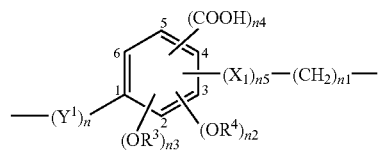
(IV)

wherein
n is an integer from 0 to 20,
n1 is an integer from 1 to 20;
n2, n3, n4 and n5 are integers equal or different from each other, equal to 0 or 1;
$R^3$ and $R^4$ are independently selected from H or $CH_3$;
$Y^1$ is —CH₂— or —(CH₂)$_{na}$—CH=CH— wherein na is an integer from 0 to 20;
$X_1$ is —WC(O)— or —C(O)W—, wherein W is oxygen, sulfur or NH.

4. A compound and the enantiomers, diastereoisomers and pharmaceutically acceptable salts thereof according to claim 3 wherein
n2, n3, n4, n5 are equal to 0,
n1 is 1,
n is an integer from 0 to 10,
$Y^1$ is $CH_2$.

5. A compound and the enantiomers, diastereoisomers and pharmaceutically acceptable salts thereof according to claim 3 wherein
n, n2, n5 are 1,
n3 and n4 are equal to 0, and
n1 is an integer from 1 to 10,
$Y^1$ is —(CH₂)$_{na}$—CH=CH— wherein na is 0,
$X_1$ is —WC(O)— wherein W is oxygen and $X_1$ is bound to the phenyl ring through the [C]₄,
$R^4$ is $CH_3$ and the group (OR⁴) is bound to the phenyl ring through the [C]₃.

6. A compound and the enantiomers, diastereoisomers and pharmaceutically acceptable salts thereof according to claim 1 wherein
Y is

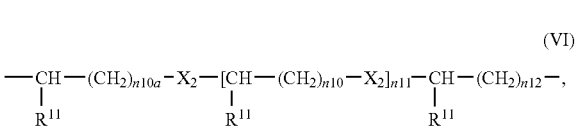
(VI)

-continued

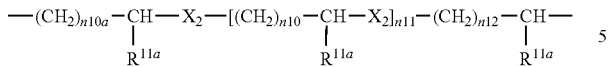 (VII)

wherein $X_2$ is O or S, n10a, n10 and n12 are integers independently selected from 0 to 20;

n11 is an integer from 0 to 6;

$R^{11}$ is H, $CH_3$ or a nitrooxy group;

$R^{11a}$ is $CH_3$ or a nitrooxy group.

7. A compound and the enantiomers, diastereoisomers and pharmaceutically acceptable salts thereof according to claim 6 wherein Y is

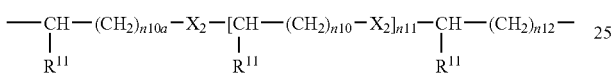 (VI)

wherein $X_2$ is O or S, n10a is an integer from 0 to 10 n11 are 0, n12 is an integer from 1 to 10, $R^{11}$ is H or a nitrooxy group;

wherein the —$ONO_2$ group is bound to the —$(CH_2)_{n12}$— group.

8. A compound and the enantiomers, diastereoisomers and pharmaceutically acceptable salts thereof according to claim 1 wherein Y is a straight or branched $C_1$-$C_{20}$ alkylene being optionally substituted with one or more of the substituents selected from the group consisting of halogen atoms, hydroxy, —$ONO_2$ or T, wherein T is —OC(O)($C_1$-$C_{10}$alkyl)-$ONO_2$, —O($C_1$-$C_{10}$alkyl)-$ONO_2$.

9. A compound and the enantiomers, diastereoisomers and pharmaceutically acceptable salts thereof according to claim 8 wherein Y is a straight or branched $C_3$-$C_6$ alkylene.

10. Compounds and the enantiomers, diastereoisomers and pharmaceutically acceptable salts thereof according to any one of claims 1, 8 or 9 wherein the compounds are:

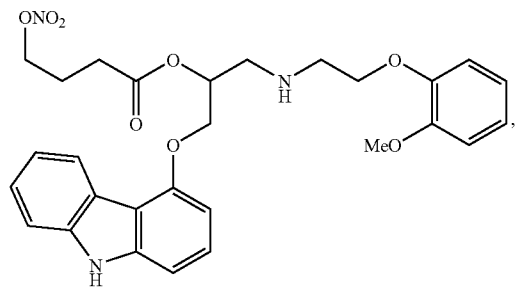 (1)

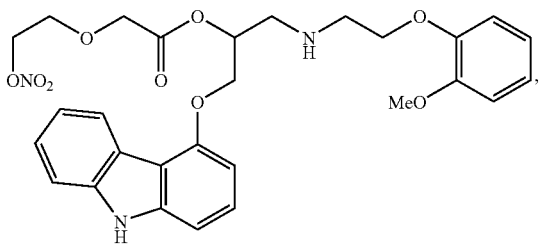 (4)

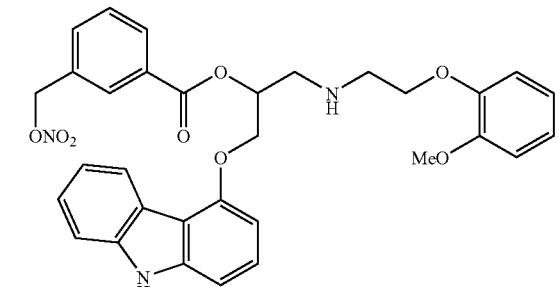 (7)

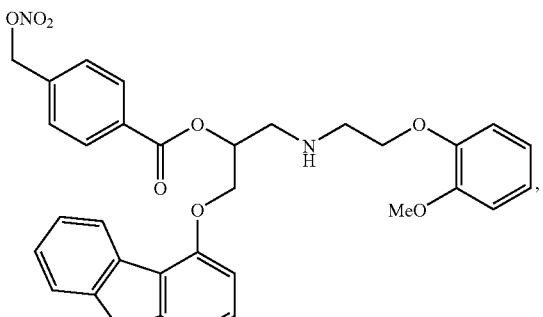 (8)

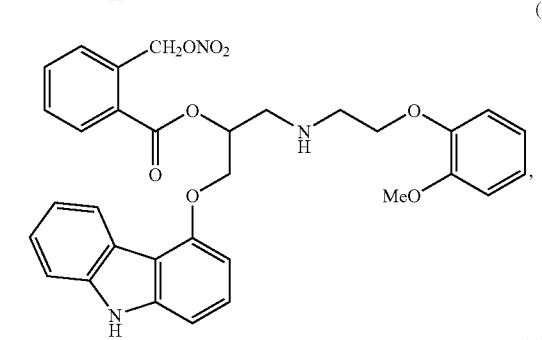 (9)

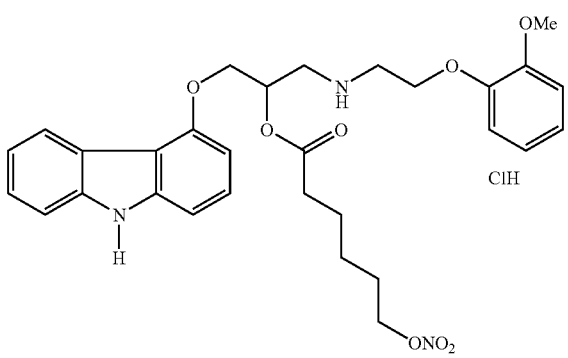 (110)

-continued

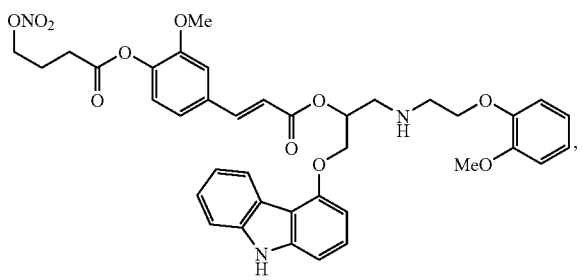

(16)

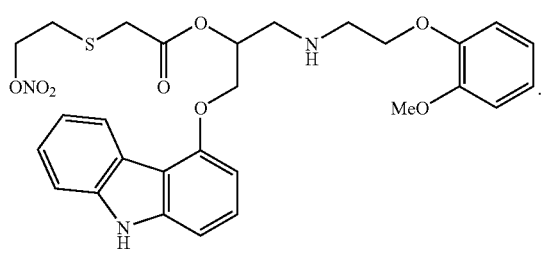

(27)

11. A compound and the enantiomers, diastereoisomers and pharmaceutically acceptable salts according to claim 1, that is 4-(Nitrooxymethyl)benzoic acid 1-(9H-carbazol-4-yloxy)-3-[[2-(2-methoxyphenoxy)ethyl]amino]-2-propanoate.

12. A compound and the enantiomers, diastereoisomers and pharmaceutically acceptable salts according to any one of claim 1, 8 or 9, that is 6-(nitrooxy)hexanoic acid 1-(9H-carbazol-4-yloxy)-3-[[2-(2-methoxyphenoxy)ethyl]amino]-2-propanol hydrochloride.

13. A medicament comprising a compound of formula (I) and/or the enantiomers, diastereoisomers and pharmaceutically acceptable salts thereof as defined in claim 1.

14. A method for the treatment or prophylaxis of hypertension, cardiovascular and vascular diseases using a drug comprising a compound of formula (I) and/or the enantiomers, diastereoisomers and pharmaceutically acceptable salts thereof as defined in claim 1.

15. A method for the treatment of glaucoma and elevated intraocular pressure using a drug comprising a compound of formula (I) and/or the enantiomers, diastereoisomers and pharmaceutically acceptable salts thereof as defined in claim 1.

16. A pharmaceutical composition comprising a compound of formula (I) and/or the enantiomers, diastereoisomers and pharmaceutically acceptable salts thereof as defined in claim 1 and at least one pharmaceutically acceptable carrier.

* * * * *

UNITED STATES PATENT AND TRADEMARK OFFICE
CERTIFICATE OF CORRECTION

PATENT NO. : 7,825,263 B2
APPLICATION NO. : 10/577912
DATED : November 2, 2010
INVENTOR(S) : Piero Del Soldato et al.

Page 1 of 1

It is certified that error appears in the above-identified patent and that said Letters Patent is hereby corrected as shown below:

Title Page: item (54) and col. 1, line 1,

Title to read as follows:

NITROOXYDERIVATIVES OF CARVEDILOL AND OTHER BETA BLOCKERS
    AS ANTIHYPERTENSIVE <u>DRUGS</u>

Signed and Sealed this
First Day of February, 2011

David J. Kappos
*Director of the United States Patent and Trademark Office*